(12) United States Patent
Estes et al.

(10) Patent No.: US 10,940,007 B2
(45) Date of Patent: Mar. 9, 2021

(54) ARTICULAR CARTILAGE REPAIR

(71) Applicant: Cytex Therapeutics, Inc., Durham, NC (US)

(72) Inventors: Bradley T. Estes, Durham, NC (US); Farshid Guilak, Durham, NC (US); Franklin Thomas Moutos, Raleigh, NC (US)

(73) Assignee: Cytex Therapeutics, Inc., Durham, NC (US)

( * ) Notice: Subject to any disclaimer, the term of this patent is extended or adjusted under 35 U.S.C. 154(b) by 146 days.

(21) Appl. No.: 16/009,496

(22) Filed: Jun. 15, 2018

(65) Prior Publication Data
US 2018/0289490 A1 Oct. 11, 2018

Related U.S. Application Data

(63) Continuation of application No. 15/288,312, filed on Oct. 7, 2016, now Pat. No. 10,022,231.

(Continued)

(51) Int. Cl.
*A61F 2/30* (2006.01)
*A61F 2/28* (2006.01)
(Continued)

(52) U.S. Cl.
CPC .......... *A61F 2/30756* (2013.01); *A61F 2/28* (2013.01); *A61L 27/18* (2013.01); *A61L 27/30* (2013.01); *A61L 27/38* (2013.01); *A61L 27/3852* (2013.01); *A61L 27/54* (2013.01); *A61L 27/56* (2013.01); *A61F 2/30* (2013.01); *A61F 2002/30062* (2013.01); *A61F 2002/3092* (2013.01); *A61F 2002/30448* (2013.01); *A61F 2002/30757* (2013.01); *A61F 2002/30766* (2013.01); *A61F 2002/30985* (2013.01);
(Continued)

(58) Field of Classification Search
CPC .............................. A61F 2/30756; A61F 2/30
See application file for complete search history.

(56) References Cited

U.S. PATENT DOCUMENTS 5,518,680 A * 5/1996 Cima ...................... A61F 2/022
264/401
5,677,355 A * 10/1997 Shalaby ................. A61K 9/122
424/486

(Continued)

*Primary Examiner* — Bruce E Snow
*Assistant Examiner* — Melissa A Hoban
(74) *Attorney, Agent, or Firm* — Maginot, Moore & Beck, LLP

(57) ABSTRACT

A method has been developed for repairing a cartilage lesion. The method includes bringing a three-dimensional porous substrate into direct contact with prepared bone. The three-dimensional porous substrate is fixedly coupled to a three-dimensional scaffold such that the substrate supports the scaffold. The three-dimensional porous substrate comprises at least three layers of woven fibers. The substrate is configured to be inserted into bone tissue including cartilage lesions such that the substrate and the scaffold replace the bone tissue including the cartilage lesions. The substrate and scaffold are further configured such that after the substrate and the scaffold have replaced the bone tissue including the cartilage lesions, the substrate and scaffold promote growth and integration of new bone tissue into the implant.

31 Claims, 14 Drawing Sheets

Related U.S. Application Data

(60) Provisional application No. 62/365,517, filed on Jul. 22, 2016.

(51) Int. Cl.
*A61L 27/18* (2006.01)
*A61L 27/30* (2006.01)
*A61L 27/38* (2006.01)
*A61L 27/54* (2006.01)
*A61L 27/56* (2006.01)

(52) U.S. Cl.
CPC ... *A61L 2300/258* (2013.01); *A61L 2300/414* (2013.01); *A61L 2430/02* (2013.01); *A61L 2430/06* (2013.01)

(56) References Cited

U.S. PATENT DOCUMENTS

| | | | | |
|---|---|---|---|---|
| 6,306,424 B1* | 10/2001 | Vyakarnam | | A61L 27/3852 424/426 |
| 6,454,811 B1* | 9/2002 | Sherwood | | A61F 2/28 623/23.76 |
| 6,530,956 B1* | 3/2003 | Mansmann | | A61F 2/30756 623/18.11 |
| 6,530,958 B1* | 3/2003 | Cima | | A61F 2/022 623/23.51 |
| 8,529,958 B2* | 9/2013 | Campbell | | A61L 27/3616 424/422 |
| 2003/0003135 A1* | 1/2003 | Leung | | B32B 5/02 424/443 |
| 2003/0006534 A1* | 1/2003 | Taboas | | A61F 2/30756 264/401 |
| 2003/0114936 A1* | 6/2003 | Sherwood | | A61F 2/28 623/23.58 |
| 2004/0062753 A1* | 4/2004 | Rezania | | A61L 27/3847 424/93.7 |
| 2004/0197367 A1* | 10/2004 | Rezania | | A61L 27/3847 424/422 |
| 2004/0236424 A1* | 11/2004 | Berez | | A61B 5/1076 623/14.12 |
| 2004/0266000 A1* | 12/2004 | Offermann | | A61L 27/3633 435/398 |
| 2005/0008675 A1* | 1/2005 | Bhatia | | B29C 67/202 424/426 |
| 2006/0195179 A1* | 8/2006 | Sun | | A61L 27/38 623/1.54 |
| 2007/0026069 A1* | 2/2007 | Shastri | | A61K 9/06 424/486 |
| 2007/0041952 A1* | 2/2007 | Guilak | | A61F 2/30965 424/93.7 |
| 2007/0224172 A1* | 9/2007 | Hendriks | | A61L 27/3817 424/93.7 |
| 2009/0043344 A1* | 2/2009 | Schlotterback | | A61F 2/30756 606/86 R |
| 2009/0208577 A1* | 8/2009 | Xu | | A61L 27/50 424/484 |
| 2009/0239302 A1* | 9/2009 | Decher | | A61L 27/34 435/402 |
| 2012/0128739 A1* | 5/2012 | Nygaard | | A61L 27/34 424/400 |
| 2013/0312897 A1* | 11/2013 | Vowles | | A61B 17/0401 156/83 |
| 2014/0242140 A1* | 8/2014 | Neu | | A61K 38/39 424/422 |
| 2015/0238318 A1* | 8/2015 | McCullen | | A61F 2/30756 623/14.12 |
| 2016/0129155 A1* | 5/2016 | Lin | | A61L 27/3834 604/21 |

* cited by examiner

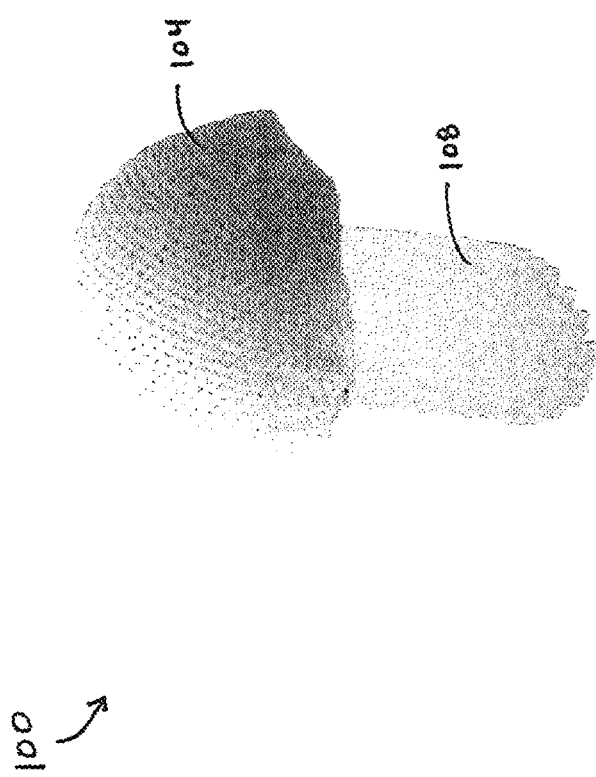

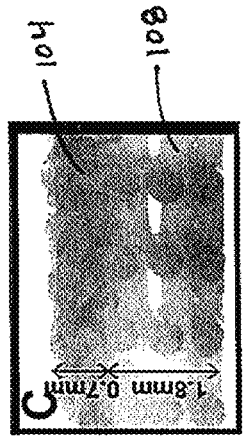
FIG. 2C
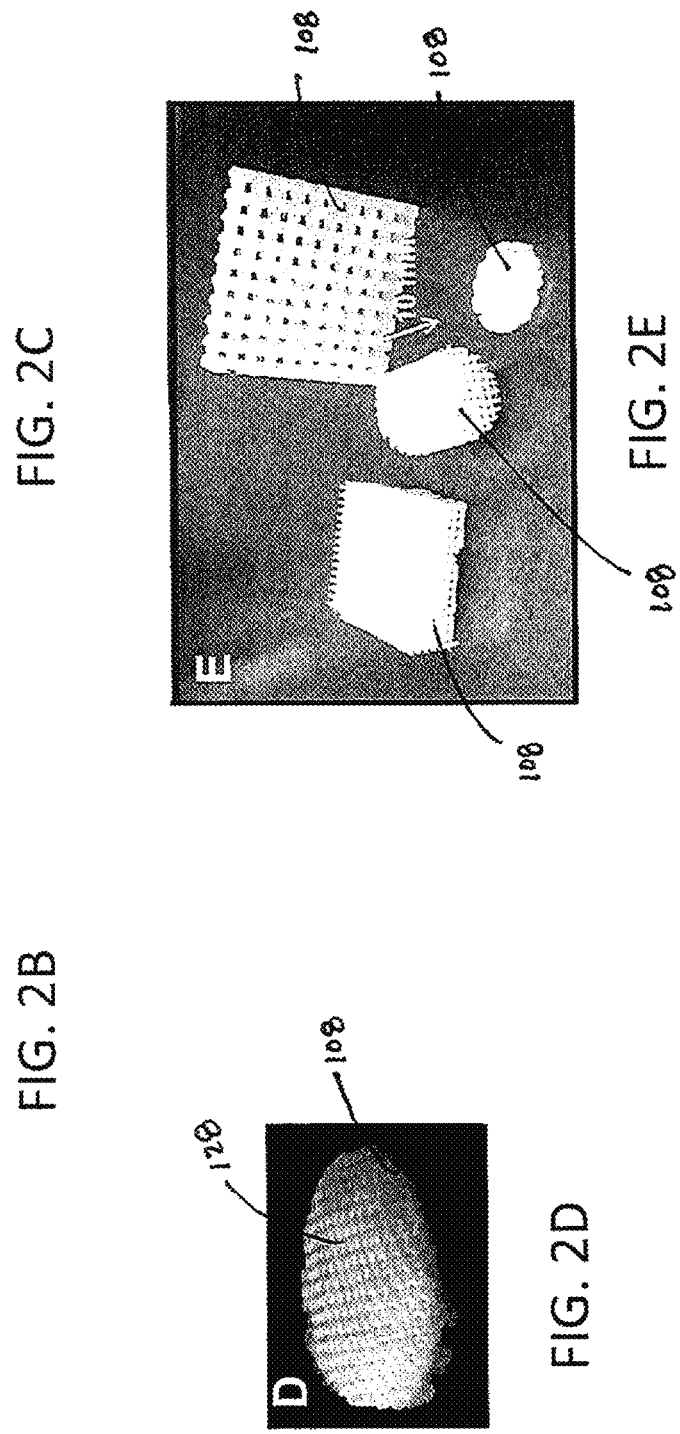
FIG. 2E
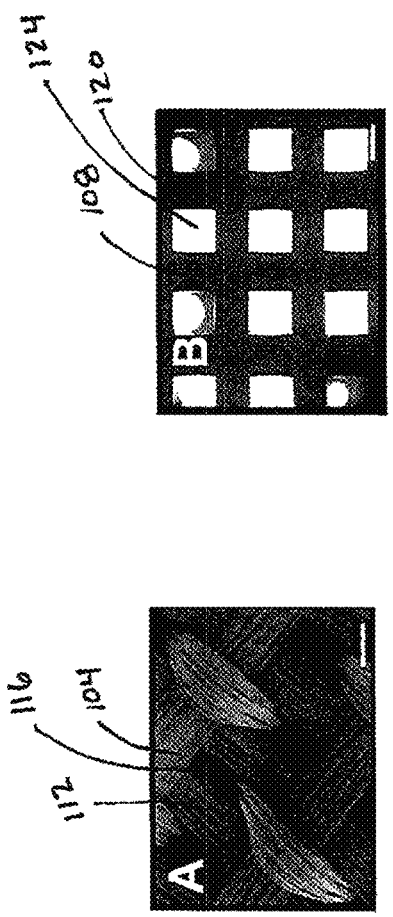
FIG. 2B
FIG. 2D
FIG. 2A

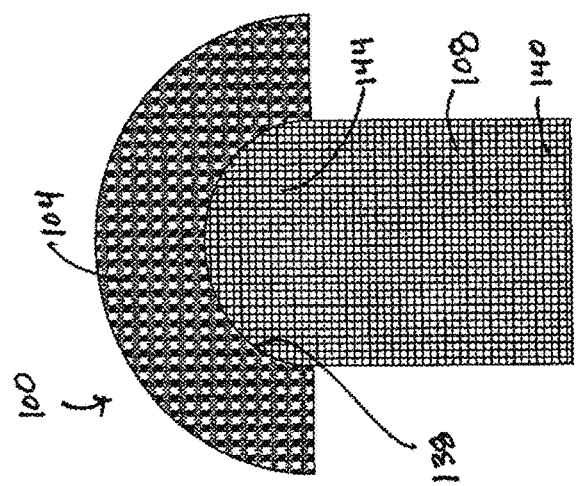
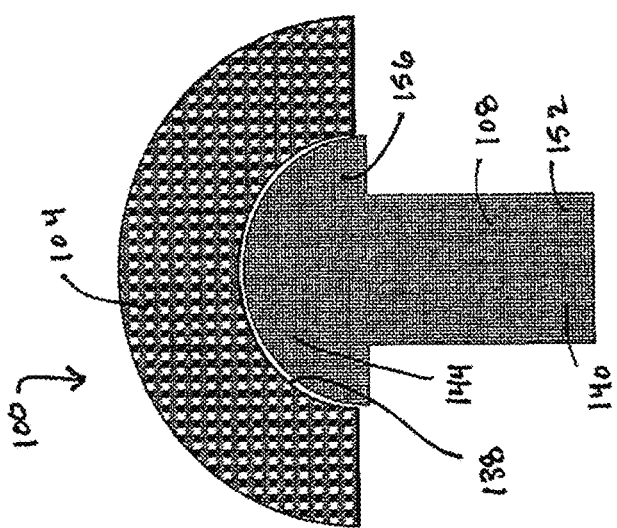
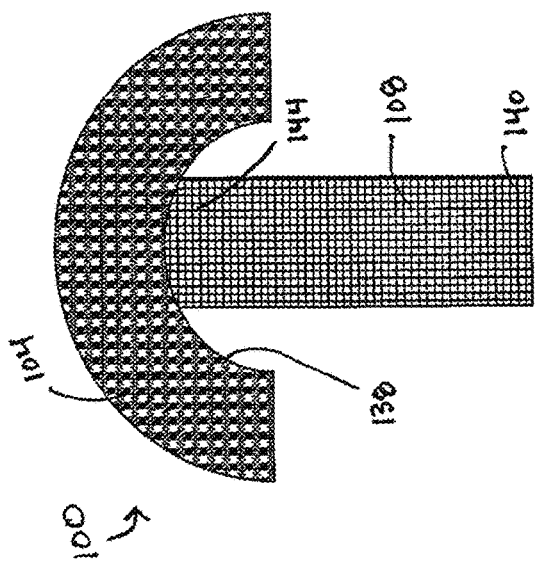
FIG. 7A
FIG. 7B
FIG. 7C

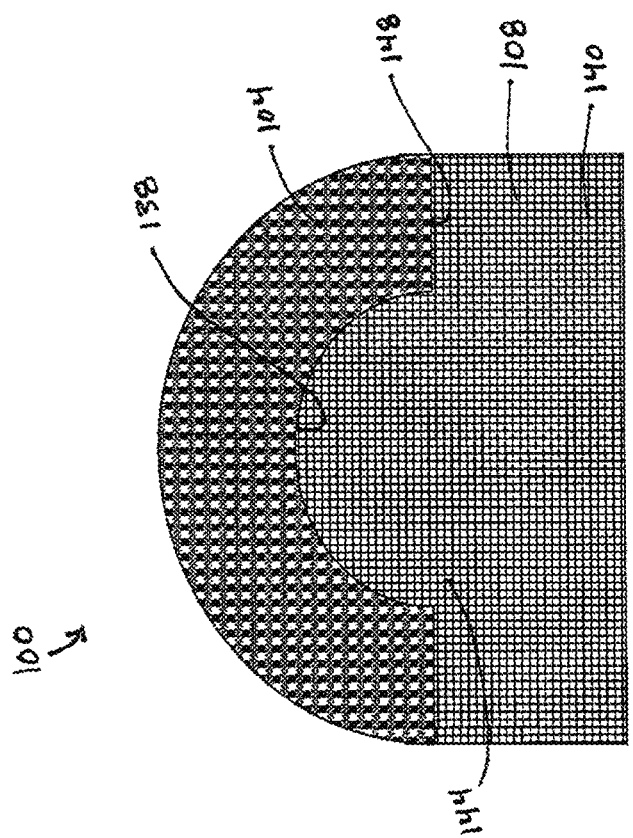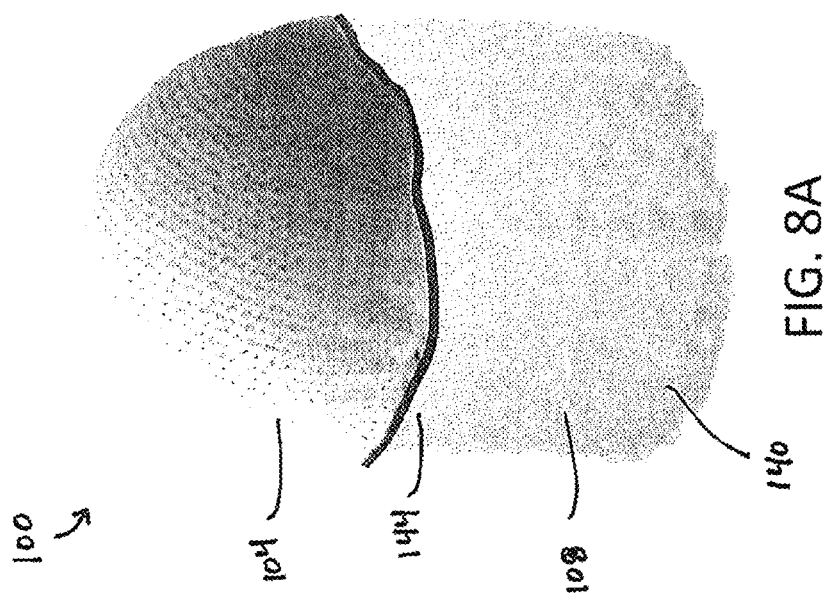
FIG. 8B
FIG. 8A

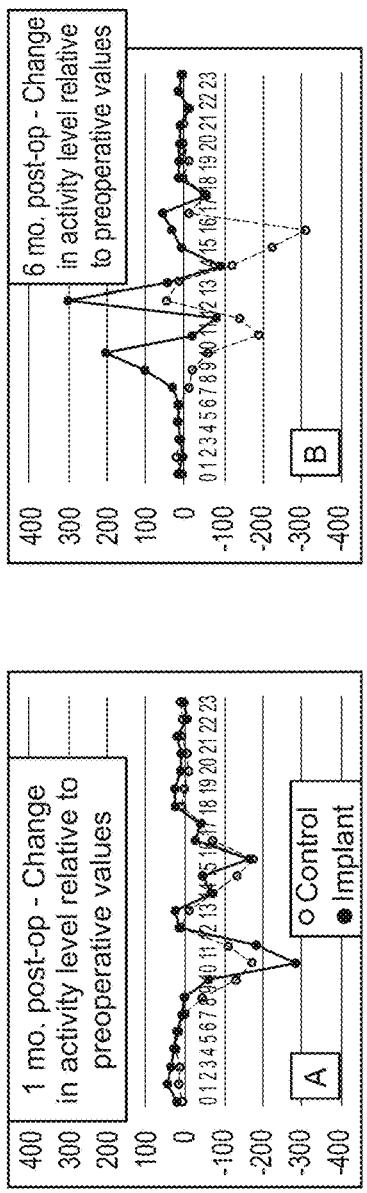
FIG. 14A
FIG. 14B
FIG. 14C
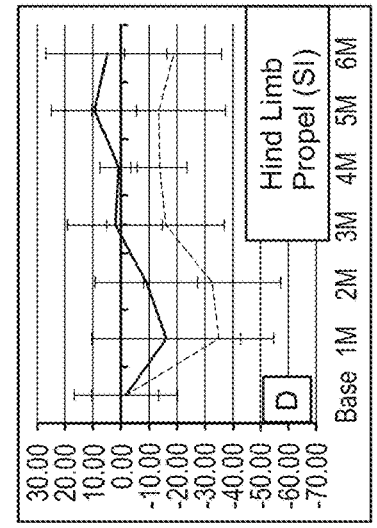
FIG. 14D
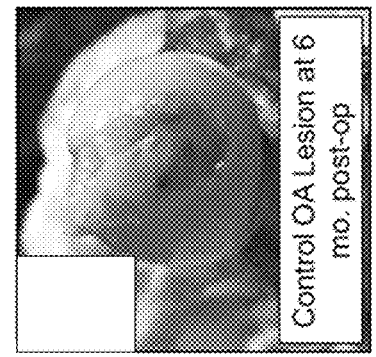
FIG. 14E
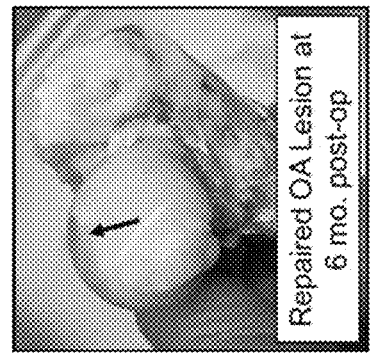
FIG. 14F

ARTICULAR CARTILAGE REPAIR

PRIORITY CLAIM

This application is a continuation of co-pending U.S. patent application Ser. No. 15/288,312, filed on Oct. 7, 2016, which claims priority to U.S. Provisional Patent Application No. 62/365,517, filed on Jul. 22, 2016, the disclosures of which are incorporated herein by reference in their entireties.

GOVERNMENT LICENSE RIGHTS

This invention was made with government support under grant R42AR055042 awarded by the United States National Institutes of Health. The government has certain rights in the invention.

BACKGROUND

Recent U.S. health statistics indicate that there are currently over 50 million individuals who have clinically diagnosed osteoarthritis, a joint disease that results from breakdown of joint cartilage and underlying bone. Furthermore, approximately 40% of this population is living with chronic joint pain. It is estimated that about 3% of the population between the ages of 40-65 (or nearly 2.8 million patients) suffers from and seeks medical treatment for hip osteoarthritis. Of these nearly 2.8 million patients, an estimated 840,000 (about 30%) suffer from activity limiting hip osteoarthritis, and it is typically these patients who are recommended for hip replacement surgery, also known as total hip arthroplasty.

Currently, it is estimated that approximately 15% of these 840,000 patients choose to undergo hip replacement surgery. This low percentage can be attributed to the relatively short projected lifetime of a hip implant for an active patient as well as the subsequent need for a revision surgery. Revision surgery, to modify a previously implanted hip implant, is associated with significant complications, co-morbidities, and overall decreased effectiveness.

Due to the lack of ideal solutions, many active patients between the ages of 40-65 are left to manage their pain through pharmaceuticals (e.g., Nonsteroidal anti-inflammatory drugs (NSAIDs)) or nutraceuticals (i.e., glucosamine and chondroitin sulfate). Thus, to address this population of active, young patients (40-65 years of age) who suffer from activity limiting hip osteoarthritis but who are not good candidates for total joint arthroplasty procedures, an approach is needed that targets the replacement of diseased cartilage (cartilage having large arthritic lesions) of the osteoarthritic, degenerated joint. Any treatment for this patient population that can stave off a traditional total hip arthroplasty procedure, provide pain relief, and restore an active lifestyle would solve a clinical problem for which no good solutions currently exist.

Many technologies have been introduced in an attempt to address this patient population. Some of these technologies include hemiarthroplasty, in which both sides of the hip joint are resurfaced or temporarily covered with metal prosthetic caps. Some implants used for hemiarthroplasty are "metal-on-metal," wherein metal is applied to both sides of the hip joint. While metal-on-metal implants used in hemiarthroplasty demonstrate good early success, recent studies have documented high levels of failure of the metal-on-metal resurfacing due to multiple factors related to excessive wear rates and increased metal debris, ultimately leading to market recalls of several of these implant systems. Similarly, it is well known that implants for hemiarthroplasty that use polyethylene surfaces, instead of metal, have been associated with implant loosening due to osteolysis secondary to particulate wear. In these cases, a revision joint replacement surgery is significantly more difficult than the original surgery and is prone to complications.

Some cartilage lesions of diseased cartilage in an osteoarthritic joint can be treated with existing cartilage repair strategies. These existing surgical "repair" strategies can generally be divided into three categories: marrow stimulation, osteochondral transfer, and autologous chondrocyte implantation or ACI (as well as Matrix assisted ACI or MACI).

ACI, made publicly available in 1995, is currently the only cell-based repair procedure for articular cartilage available for clinical use in the United States. This procedure involves isolation and amplification of the patient's own chondrocytes, followed by re-implantation of cells into the cartilage defect, which is then covered by a flap of the patient's own periosteal tissue. Although clinical outcomes have been reported as good to excellent, several complications, such as graft overgrowth and the presence of loose bodies, have been reported in a significant number of patients. A number of these problems are arguably related to the lack of a scaffolding biomaterial, which would help retain cells at the site of implantation, guide and constrain the growth of the tissue, promote integration with the host cartilage, and provide the biological signals (whether endogenous or therapeutically-embedded) required for proper growth and differentiation. Unfortunately, one consistent exclusion criteria, which prevents patients from being eligible for existing cartilage repair strategies, is diffuse osteoarthritis or large areas of diseased cartilage. Accordingly, there may be defined windows of time, in which current strategies may be utilized to treat acute cartilage pathology to inhibit altogether or delay the progression to osteoarthritis.

A brief review of relevant literature indicates successful clinical results for these three broad categories of cartilage repair, albeit with overarching caveats, namely: (1) no diffuse osteoarthritis; (2) no concomitant instability; (3) patients should be younger than 45 years old; and (4) the lesions should be smaller than 4 $cm^2$.

In an attempt to expand the use of existing cartilage repair techniques, there have been several studies undertaken to treat osteoarthritis in this young patient population. Osteochondral transfer, along with microfracture procedures have been attempted with larger lesions, and have clearly demonstrated inferior results relative to the treatment of smaller, contained lesions. Recent efforts have also involved extending the inclusion criteria of the second generation ACI or MACI procedure in order to treat chronic disease in young patients. A high failure rate of 27.3% has been reported in young patients treated with the MACI procedure after a 9-year mean follow-up. Similarly, poor results and a large percentage of failure have been reported in young patients treated with the ACI technique in osteoarthritis situations. Taken together, these results suggest a demanding joint environment for tissue engineering strategies and a need for materials with appropriate mechanical properties to not only survive in the joint but also to support and promote a regenerative response for long-term functionality.

Because of the unmet clinical need to repair and regenerate articular cartilage, there continues to be a significant interest in improved tissue engineering strategies for this purpose. This interest has escalated in the last 15 years, resulting in more than 20 cartilage tissue engineering products focused on focal defect repair that are in various stages of development or approval. These products focus largely on the use of biomaterials that improve upon methods to trap cells within a defect. Others have focused on creating bilayer osteochondral implants to recreate the bilayer structure of osteochondral tissue, but are not able to replicate the mechanical properties of the native tissues.

Relevant literature is replete with other approaches to grow functional tissues in vitro, which have been and are currently being explored in the research setting, using both synthetic and natural polymeric materials. Such approaches include using fibrous meshes and foams made of biodegradable ß-hydroxy esters (e.g., polyglycolic acid and polylactic acid), peptide-modified polymers, collagen, hyaluronic acid, and chitosan, along with macroporous hydrogels of agarose and alginate. Such scaffold designs have been generally successful in forming structures histologically similar to cartilage. It has proven more difficult, however, to effectively recreate both the biomechanical and biochemical function of the natural tissue, particularly at early times after implantation. For example, the initial (i.e., post-culture, pre-implantation) mechanical properties of biodegradable polymer constructs have tended to be too stiff, while conversely, seeded hydrogels at the same stage have displayed insufficient stiffness, especially in tension, which is required to enable fluid pressurization and load support. It has been suggested that an idealized scaffold should be stiff enough to withstand the expected in vivo loading while allowing, and even promoting, the biosynthesis of functional tissue within the scaffold. Because currently existing products do not replicate the functional properties of the native tissues, they can only be used for small lesions, not large, degenerated cartilage surfaces.

U.S. Pat. No. 8,691,542 discloses a three-dimensional woven scaffold for cartilage tissue resurfacing. The three-dimensional woven scaffold is used to resurface a number of defects in the cartilage surface by replacing the articular cartilage surface. However, the three-dimensional scaffold in the '542 patent does not employ an anchoring means, and does not incorporate a shape maintaining and anchoring layer.

Other references have disclosed the use of multiphasic materials for the use of osteochondral tissue engineering. U.S. Pat. Nos. 7,776,100 and 7,963,997 disclose a cartilage region comprising a polyelectrolytic complex joined with a subchondral region with a hydrophobic barrier between the regions, wherein the polyelectrolytic complex transforms to a hydrogel. U.S. Pat. No. 6,319,712 discloses a biohybrid articular surface replacement in the form of a three-dimensional, porous carrier for cell growth and tissue development with a separate agent for aiding in osseous integration.

U.S. Pat. No. 6,306,169 discloses a biomechanical implant that is composed of two matrix components: the first component composed of a collagen, and the second component composed of a hydrated alginate for use in damaged cartilage tissue. U.S. Pat. No. 5,607,474 discloses a carrier for supporting replenished tissue growing in a diseased or damage system of a region of tissue having different mechanical properties. This patent discloses two porous layers that are amenable to tissue growth of the two different layers of tissue with corresponding mechanical properties of the two disparate tissue layers. U.S. Pat. No. 7,217,294 discloses the use of a two or three dimensional biodegradable scaffold implanted in the osteochondral lesion below one or more layers of sealants, wherein the sealants separate the layers of bone and cartilage.

U.S. Pat. No. 5,842,477 discloses the implantation of a three-dimensional scaffold structure in combination with periosteal or perichondrial tissue for the purposes of cartilage repair. U.S. Pat. No. 9,072,815 discloses a multilayered collagen scaffold suitable for osteochondral tissue repair comprising a first layer of type I collagen and hyaluronic acid, a second layer comprising a mixture of type I and II collagen and hyaluronic acid and a third layer of type I and type II collagen and another polymer or biologic (e.g., glycosaminoglycan).

U.S. Pat. No. 8,685,107 discloses a double-structured tissue implant comprising a primary scaffold with a plurality of pores and a secondary cross-linked collagenous scaffold within said pore structure for the repair of cartilage defects. This is a single-phase (i.e., one structure consisting of the combination of two materials) composite material for the purposes of cartilage repair and thus seeks the restoration of the cartilage layer upon implantation. Similarly, U.S. Pat. Nos. 8,192,759, 8,444,968, 8,512,730, and 8,580,289 disclose a single phase implant for osteochondral (as well as using the same material for other tissues) repair with a matrix comprising a polyester polymer entangled with a polysaccharide polymer.

U.S. Pat. No. 5,736,372 discloses cells mixed with a biocompatible matrix consisting of polymer fibers, incubated in vitro, and then implanted into the cartilage defect to ultimately form a cartilaginous structure in vitro. This is also a single-phase mixture for articular cartilage repair.

U.S. Pat. No. 8,226,715 discloses a plurality of three-dimensional woven bioresorbable fibers for the purposes of tendon and ligament reconstruction. The woven structure is one method of anchoring the tendon/ligament repair device into the bone in which the three-dimensional woven construct is not intended to incorporate into bone but rather relies on the rigid, porous, shape-maintaining structure to which the three-dimensional woven layer is bonded.

The aforementioned patents disclose methods and implants for treating cartilage defects, and many rely on at least two different components in a layered approach (biphasic or triphasic) to repair the osteochondral lesion (i.e., bone and cartilage). The prior art does not contain an ordered, woven matrix and does not provide anchoring, shape-maintaining features.

SUMMARY

This disclosure addresses these issues by utilizing a three-dimensionally woven scaffold system with engineered, bio-mimicking mechanical properties for functional cartilage regeneration. The presently disclosed methods and implants rely principally on a biomimetic three-dimensional woven construct to replace the articular cartilage layer. To this layer, an anchoring substrate is added that effectively incorporates a rigid, shape-defining, porous substrate to the textile-based cartilage resurfacing layer.

The problem of regenerating, restoring, and/or replicating functional tissues in the joint requires an implant that is engineered specifically for joint reconstruction. The cartilage repair implant disclosed herein immediately replicates the load-bearing properties of the articular cartilage tissues and spatially controls tissue development by means of the porous, rigid, anchoring substrate. This biomimetic, anatomically correct implant can be customized to "exactly fit" each lesion, thereby providing three important features: 1) the ability to precisely restore the specific contour of each patient's cartilage and thus joint congruity, 2) the ability to provide a seamless "press fit" to secure the full thickness cartilage implant without the need for additional sutures, screws, or fibrin glue used in other procedures, and 3) as large cartilage lesions often involve degeneration of the underlying bone (e.g., sclerotic bone), using a porous base as an anchor has the added benefit of replacing this "diseased" bone.

Immediately upon implantation, the implant provides tensile, compressive, and shear properties similar to those of native cartilage, prior to the influx of cells and development of tissue on the implant, while also being solidly anchored in the underlying bone. This anchor provides a solid base for the three-dimensional woven cartilage layer, assists in maintaining joint congruity, and is readily incorporated into the underlying, surrounding bone. In so doing, the implant addresses the deficiencies of current clinical treatment options. Furthermore, this approach maintains existing bone-stock if conversion to a total joint arthroplasty (TJA) becomes necessary later in life. As such, this implant enables delaying the time to TJA and can provide a major benefit for the treatment of common femoral cartilage disorders by restoring joint form and function, providing pain relief, and returning patients to an active lifestyle.

The present disclosure is directed to methods and systems for articular cartilage repair for restoring native structure and function to tissues that have been lost or degenerated due to osteochondral lesions. The present disclosure introduces a porous, rigid substrate coupled to three-dimensional microwoven textiles to create high-performance, precisely engineered structures that can be used to treat large cartilage lesions by providing native cartilage function and accurate maintenance of joint congruity immediately after implantation. Herein, we disclose use of a hybrid structure consisting of a three-dimensional woven textile on a three-dimensional porous, rigid material.

The addition of the porous substrate to the three-dimensional woven textile presents a substantial improvement to the ability of the three-dimensional woven construct to repair, replace, and/or regenerate large areas of pathologic articular cartilage. The textile is engineered to mimic many of the loadbearing mechanical properties of cartilage, and the substrate anchors the three-dimensional woven scaffold to rigidly define the shape needed for a successful, functioning clinical outcome. In this way, the substrate defines or assists the maintenance of anatomic shape of the textile while the cartilage is being regenerated and/or repaired.

The novelty of this structure stems from its ability to be used as an implant to resurface large areas of degenerated cartilage in the joint while restoring and maintaining joint anatomy and congruity. Resurfacing a large area is in direct contrast to treating isolated, focal defects of the articular cartilage. The textile is fabricated using a three-dimensional orthogonal fiber weaving technology to produce a biomimetic scaffold, which replicates many of the inhomogeneous, anisotropic, and viscoelastic mechanical properties of articular cartilage. The textile is bonded to the three-dimensional printed substrate, effectively creating a cartilage repair implant that can be used for large areas of joint damage, erosion, and/or degeneration. The resulting architecture effectively provides a high performance implant that recreates the physical and structural properties of the native tissue while providing a solid anchor point into the subchondral bone for implant stability and immobilization.

BRIEF DESCRIPTION OF THE DRAWINGS

FIG. 1 depicts a cartilage repair implant including a three-dimensional scaffold and a three-dimensional substrate.

FIG. 2A shows a scanning electron micrograph of a surface of the three-dimensional scaffold of the cartilage repair implant of FIG. 1.

FIG. 2B shows a top-down stereomicroscope image of the three-dimensional substrate of the cartilage repair implant of FIG. 1.

FIG. 2C shows a cross-section of the three-dimensional scaffold and the three-dimensional substrate of FIG. 1.

FIG. 2D shows an exemplary shape of the cartilage repair implant of FIG. 1.

FIG. 2E shows alternative exemplary shapes of the three-dimensional substrate of the cartilage repair implant of FIG. 1.

FIG. 7A shows one embodiment of the three-dimensional substrate of the cartilage repair implant of FIG. 1.

FIG. 7B shows another embodiment of the three-dimensional substrate of the cartilage repair implant of FIG. 1.

FIG. 7C shows another embodiment of the three-dimensional substrate of the cartilage repair implant of FIG. 1.

FIG. 8A depicts an alternative embodiment of the cartilage repair implant of FIG. 1.

FIG. 8B depicts a cross-sectional view of the cartilage repair implant of FIG. 8A.

FIG. 14A depicts a graph of activity levels of a canine model one month after implantation of an implant such as the cartilage repair implant of FIG. 1.

FIG. 14B depicts a graph of activity levels of a canine model six month after implantation of an implant such as the cartilage repair implant of FIG. 1.

FIG. 14C depicts a graph of peak vertical force of a canine model after implantation of an implant such as the cartilage repair implant of FIG. 1.

FIG. 14D depicts a graph of hind limb propel force of a canine model after implantation of an implant such as the cartilage repair implant of FIG. 1.

FIG. 14E depicts a control model of bone tissue including a cartilage lesion six months after an operation.

FIG. 14F depicts an experimental model of bone tissue including a cartilage lesion that was replaced by an implant such as the cartilage repair implant of FIG. 1 six months after an implantation operation.

DETAILED DESCRIPTION

Figure 3A:
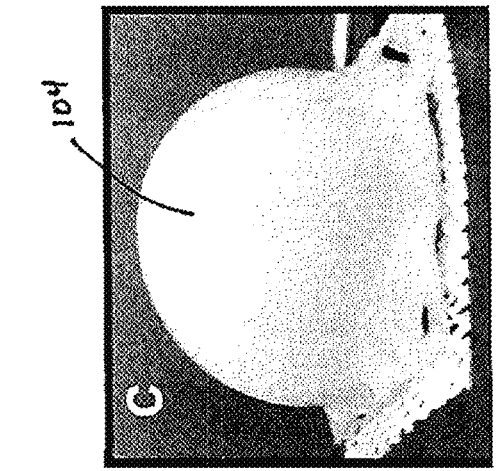
FIG. 3A a schematic illustration of a microwoven structure of the three-dimensional scaffold.

For the purposes of promoting an understanding of the principles of the invention, reference will now be made to the embodiments described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Most biomaterials used for cartilage tissue engineering do not possess the mechanical properties and load-bearing characteristics of native cartilage until significant matrix deposition has occurred over time, and thus may require significant ex vivo culture before implantation. U.S. Pat. No. 8,691,542 discloses a three-dimensional "microweave" of fibers in three orthogonal directions. This process is superior to standard weaving methods because it eliminates fiber crimp and forms a true three-dimensional structure. (In comparison, most current three-dimensional textile composite materials are constructed by laminating multiple 2D structures together, and the interface between multiple layers is the weak point in the composite where delamination can occur.) Furthermore, the controlled regularity and interconnectivity of the resulting pore structure allows cells to be easily loaded and uniformly distributed within the scaffold upon which they are able to synthesize a robust extracellular matrix (ECM). The regular pore geometry also has a positive effect on tissue maintenance by facilitating nutrient diffusion along regular and continuous paths throughout the scaffold.

In the present disclosure, the three-dimensional microweave of fibers has been optimized to mimic the functional properties of articular cartilage and has demonstrated the ability to sustain functional properties over extended in vitro culture. Specifically, the three-dimensional microweaves disclosed herein show strong tension-compression nonlinearity, with a difference of 2-3 orders of magnitude in tensile and compressive moduli, similar to native cartilage. Furthermore, they show significant fluid load support with an apparent hydraulic permeability of $10^{-15}$ m$^4$/N-s, also similar to that of native cartilage. In a preferred embodiment, the scaffold disclosed herein is constructed with bioresorbable materials but may be also constructed with non-resorbable materials as well. In either case, the three-dimensional microweave must be constructed with the appropriate material, filament diameter, yarn diameter, fiber spacing, and weaving parameters necessary to produce an implant with constitutive properties consistent with cartilage.

In the present invention disclosure, as shown in FIG. 1, an implant 100 includes a three-dimensional microwoven textile scaffold 104, used for cartilage repair, fixedly coupled to a porous, rigid substrate 108. In at least one embodiment, the scaffold 104 can be thermally bonded to the substrate 108. In at least one alternative embodiment, the scaffold can be attached to the substrate 108 with medical grade adhesive. The rigid substrate 108 enables effective securing of the implant 100 to a site of pathology, and, since the anchoring rigid substrate 108 can be manufactured in any shape and size, while still maintaining its porous architecture, the anchoring rigid substrate 108 assists in maintaining appropriate anatomical geometry so that the mechanically functioning implant 100 can perform as native, anatomic tissues.

As shown in FIG. 2A, the three-dimensional woven textile scaffold 104 of the cartilage repair implant 100 is a three-dimensional microweave structure of fibers 112 forming pores 116 therebetween. The woven textile scaffold 104 has a controlled porosity, and the pores 116 are, for example, approximately 50 μm to approximately 1000 μm to allow through-growth and consolidation of tissue in the implant 100. In at least one embodiment, the pores 116 can be approximately 100 μm to approximately 500 μm. In at least one embodiment, the pores 116 can be approximately 250 μm to approximately 400 μm.

The fibers 112 of the woven textile scaffold 104 are made from biocompatible materials, which may be multifilament fibers, monofilament fibers, filaments that have variable or irregular cross-section along their lengths, hollow fibers, or any combination thereof. The fibers 112 are, for example, approximately 25 μm to approximately 300 μm in thickness or diameter. The biocompatible fibers 112 are comprised of bioresorbable biomaterials, non-bioresorbable biomaterials, or combinations thereof. Representative non-bioresorbable materials include but are not limited to polypropylene, polyester, polytetrafluoroethylene (PTFE), polyurethane, polycarbonate urethane, polyamide, nylon, polyaryletherketone materials (PAEK), polysulfone, carbon, ceramic, metal, or any other acceptable non-bioresorbable biomaterial fiber. Representative resorbable materials include but are not limited to polyglycolic acid (PGA), polylactic acid (PLA), polycaprolactone (PCL), collagen, silk, chitin, chitosan, hyaluronic acid, or any other acceptable bioresorbable biomaterial fiber.

As shown in FIG. 2B, the rigid substrate 108 of the implant 100 includes struts 120, which define pores 124 therebetween. The struts 120 of the rigid substrate 108 can preferably be formed by three-dimensional plotting/printing a polymer, for example, plotted/printed poly(e-caprolactone) (PCL). PCL is a beneficial material to use because it enables maintenance of the proper geometry in the joint, and because bioplotted PCL with pores of 100-500 µm can promote osteogenesis of transplanted stem cells by stimulating signaling pathways that enhance osteogenesis. Accordingly, a rigid substrate 108 having struts 120 formed from bioplotted PCL with pores 124 of 100-500 µm can further assist in long term maintenance of the anchoring function of the rigid substrate 108.

It is possible for deep bone lesions to be associated with the cartilage lesion to be treated with the implant 100, and, although bone tissue has the capacity for self-regeneration, when a subchondral defect is large or deep, it will frequently remain unrepaired unless suitable bone void fillers are used. In this case, the rigid substrate 108, having appropriate geometry and pore sizes provided by the struts 120 and pores 124, provides the necessary mechanical and structural properties of a successful bone void filler.

The size of the pores 124 becomes more important in vivo as it influences processes such as cell infiltration and subsequent vascularization of the substrate 108. The biocompatible struts 112 of the substrate 108 are comprised of bioresorbable biomaterials, non-bioresorbable biomaterials, or combinations thereof. Representative non-bioresorbable materials include but are not limited to polypropylene, polyester, polytetrafluorethylene (PTFE), polyurethane, polycarbonate urethane, polyamide, nylon, polyaryletherketone materials (PAEK), polysulfone, carbon, ceramic, metal, or any other acceptable non-bioresorbable biomaterial filament. Representative resorbable materials include but are not limited to polyglycolic acid (PGA), polylactic acid (PLA), polycaprolactone (PCL), collagen, chitin, chitosan, or any other acceptable bioresorbable biomaterial filament.

In at least one embodiment, the cartilage repair implant 100 can also deliver cells (e.g., chondrocytes, fibroblasts, progenitor cells, stem cells, reprogrammed cells) and/or additional, exogenously introduced biologically active molecules, such as growth factors, cytokines, chemokines, antibiotics, DNA, plasmids, or other molecules that may induce directed growth and/or differentiation of cells, or vectors capable of delivering bioactive therapeutic genes to the product. In particular, the textile scaffold 104 and/or the substrate 108 may be used to deliver different cells, molecules, growth factors, cytokines, chemokines, antibiotics, DNA, plasmids, or other molecules that may induce directed growth and/or differentiation of cells, or vectors capable of delivering bioactive therapeutic genes to the product. The substrate 108 of the implant 100 and/or part of the three-dimensional woven scaffold 104 may be at least partially coated with inorganic matrix coatings known to promote bone formation such as, hydroxyapatite, calcium phosphate, calcium carbonate, alumina, zirconia, yttria-stabilized zirconia, silicon nitride-based materials, bioactive glass, and/or glass ceramics. One or both of the textile scaffold 104 and the substrate 108 may also be at least partially coated with extracellular-derived biomaterials such as a cartilage-derived matrix, demineralized bone matrix or other decellularized tissues. In another embodiment, the implant 100 can be partially (e.g., on the side of the textile scaffold 104) or completely filled with a biomaterial gel consisting of collagen, hyaluronic acid, alginate, agarose, chitosan, gelatin, laminin, fibronectin, interpenetrating networks (networks that are completely biological, all synthetic, or a combination of the two), or fibrin.

In yet another alternative embodiment, the fibers 112 of the implant 100 can be coated with bioactive coatings, for example adeno-associated virus (AAV), lentivirus (LV), naked DNA, peptides, self-assembling peptides, anti-inflammatory drugs, cytokines, cytokines inhibitors, macromolecules native to bone and cartilage (e.g., proteoglycan, cartilage oligomeric matrix protein, hyaluronic acid, collagen type I, collagen type II, and bone morphogenetic proteins) or a combination thereof. A portion of the fibers 112 may be coated with one or more biological agents, and portions may be left uncoated or coated with altogether different agents. One of the benefits of the architecture of warp interlock fabrics such as the woven textile scaffold 104 is the ability to coat individual fiber bundles to induce site-specific differentiation of cells on the scaffold 104.

Referring to FIG. 2A, a scanning electron micrograph of a surface of the three-dimensional woven textile scaffold 104 is shown. The scaffold 104 is formed from PCL (scale bar=0.2 mm). FIG. 2B shows a top-down stereomicroscope image of the rigid substrate 108 of the cartilage repair implant 100. The struts 120 of the rigid substrate 108 are stacked in alternating 0 and 90 degree alignment (scale bar=0.5 mm). In an alternative embodiment, the struts 120 can be stacked at angles of approximately 30 degrees to approximately 120 degrees relative to one another.

FIG. 2C shows a cross-section of the textile scaffold 104 and the rigid substrate 108 of the cartilage repair implant 100. FIG. 2D illustrates that the rigid substrate 108 of the implant 100 can be manufactured in different shapes, for example, in anatomic shapes, to assist in anchoring the implant 100 in a particular site. In particular, FIG. 2D depicts a 10 mm diameter cartilage repair implant 100 with an anatomic, domed surface 128 configured to match the curvature of a 24 mm diameter femoral head. FIG. 1E further depicts alternative embodiments of the rigid substrate 108 that are three-dimensional printed in various sizes and shapes for different particular applications.

Figure 3B:
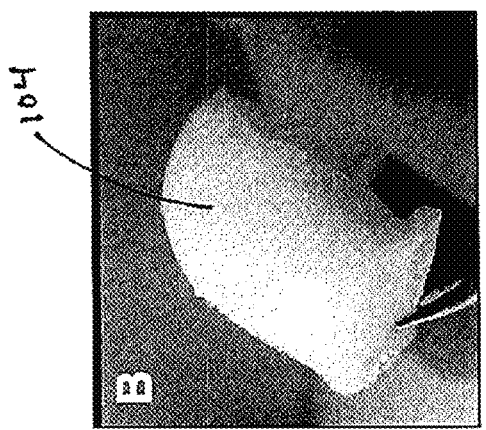
FIG. 3B depicts an example of the three-dimensional scaffold of FIG. 1 molded into a particular anatomic shape.
Figure 3C:
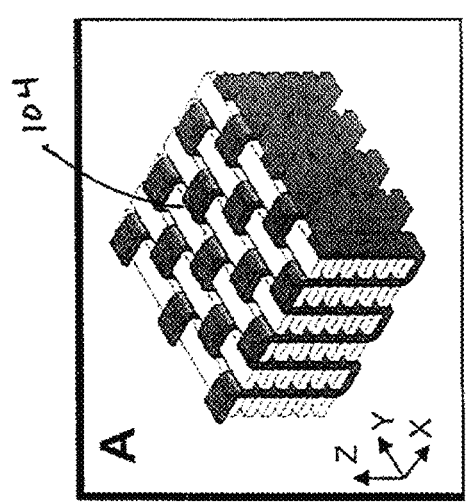
FIG. 3C depicts an example of the three-dimensional scaffold of FIG. 1 molded into an alternative particular anatomic shape.
Figure 3D:
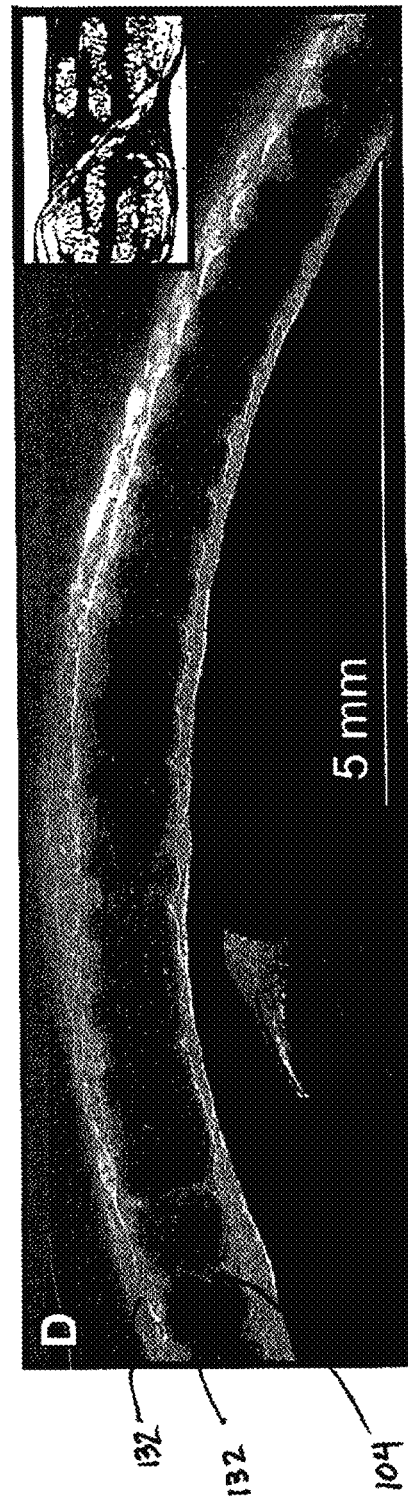
FIG. 3D depicts live cells in and on the three-dimensional scaffold of FIG. 1.

FIGS. 3A-3D illustrate the efficacy of the textile scaffold 104 in regenerating cartilage tissue in vitro. FIG. 3A is a schematic illustration of the three-dimensional microwoven structure of the textile scaffold 104. FIGS. 3B and 3C are examples of the textile scaffold 104 that have been molded into anatomic shapes and then cultured ex vivo. In the example shown in FIG. 3B, the textile scaffold 104 is shown without the rigid substrate 108. The textile scaffold 104 is formed from PCL and molded in the shape of a femoral condyle. In the example shown in FIG. 3C, the textile scaffold 104 is formed from PCL and molded in the shape of a femoral head. The molded PCL scaffolds 104 shown in both of FIGS. 3B and 3C were cultured in chondrogenic conditions for 4 weeks, and thus developed the smooth surface seen in the figures from tissue development on the scaffold. FIG. 3D shows a cross-sectional confocal image after 5 weeks.

The image of FIG. 3D depicts live cells 132 embedded within an ECM and fully encapsulating the scaffold 104. Thus, the image of FIG. 3D further demonstrates robust tissue development within the three-dimensional porous architecture of the scaffold 104. The inset shown on the left of FIG. 3D depicts a magnified view, which demonstrates tissue development in the pore structure of the scaffold 104. The inset shown on the right of FIG. 3D depicts immunolabeling for type II collagen, which demonstrates significant deposition of the principal collagen found in articular cartilage.

Figure 4B:
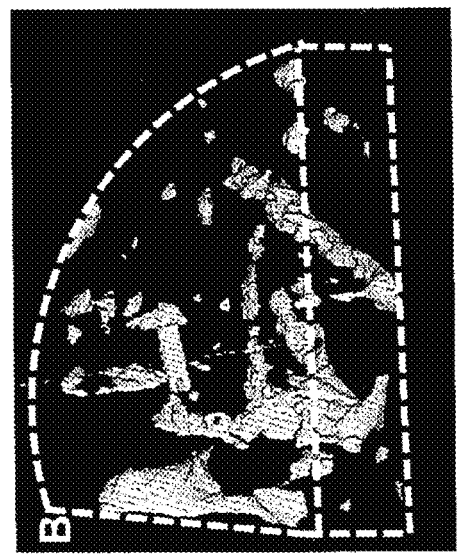
FIG. 4B depicts a CT reconstruction of the three-dimensional scaffold of FIG. 1.
Figure 4A:
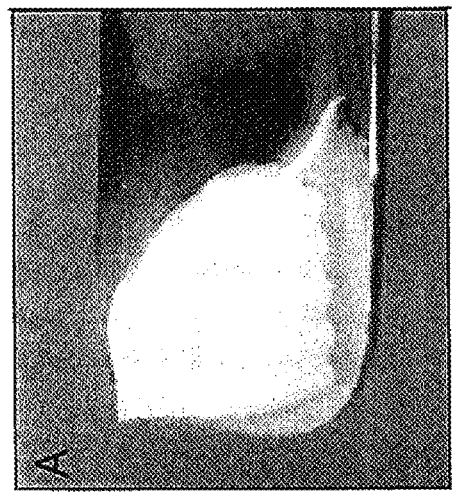
FIG. 4A depicts the three-dimensional scaffold of FIG. 1 ex vivo.

FIGS. 4A and 4B depict a three-dimensional printed scaffold 104 that is seeded with stem cells and cultured ex vivo in osteogenic media for 6 weeks. FIG. 4A shows the gross image at 6 weeks, and FIG. 4B reveals scaffold mineralization in the CT reconstruction.

Figure 5B:
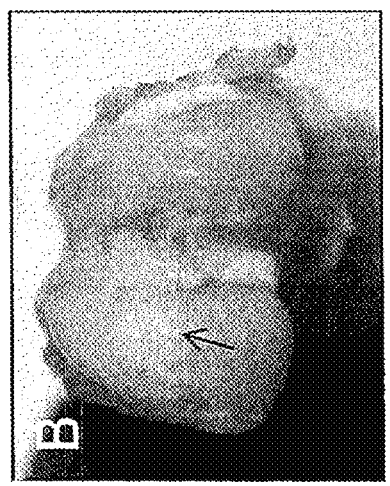
FIG. 5B depicts the three-dimensional scaffold of FIG. 1 implanted into bone tissue.
Figure 5D:
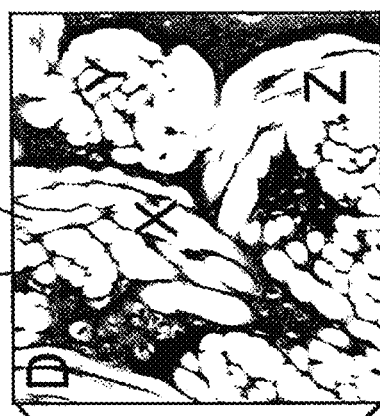
FIG. 5D depicts a closer view of a portion of the three-dimensional scaffold of FIG. 5C.
Figure 5C:
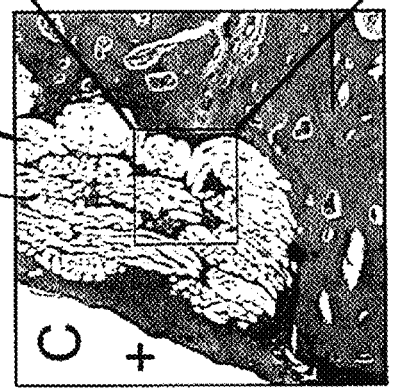
FIG. 5C depicts the three-dimensional scaffold of FIG. 1 in vivo.
Figure 5A:
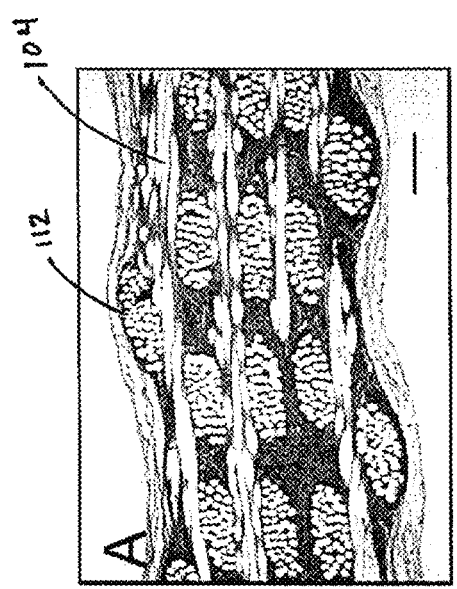
FIG. 5A depicts the three-dimensional scaffold of FIG. 1 in vivo.

Studies conducted using various animal models assess the capacity of the implant 100 to support tissue growth and development in vivo. In early studies, cell infiltration, tissue ingrowth, and attachment of the three-dimensional woven scaffold 104 to host tissues was demonstrated when implanted acellularly for 8 weeks in a rat ectopic model. Subsequent to this study, robust tissue synthesis was shown in a rabbit model for articular cartilage repair when implanted acellularly in an osteochondral defect in the medial condyle of a rabbit. In this lapine model, rapid and complete integration of surrounding native tissue was specifically noted as early as 6 weeks with no evidence of fibrous encapsulation and/or gaps between native bone or native cartilage. Importantly, the scaffold fibers 112 (all white, non-stained sections in FIGS. 5A, 5C, and 5D are bundles of scaffold fibers 112) in both species remained intact to provide a "functional" implant while guiding and supporting tissue growth. Not only did the constructs demonstrate robust levels of biosynthetic activity within the scaffold 104, but the constructs also supported a strong chondrogenic phenotype as evidenced by Safranin-O staining (FIGS. 5C and D) throughout the structure of the scaffold 104. Note that these early studies did not incorporate the rigid substrate 108 of the implant 100.

Figure 6A:
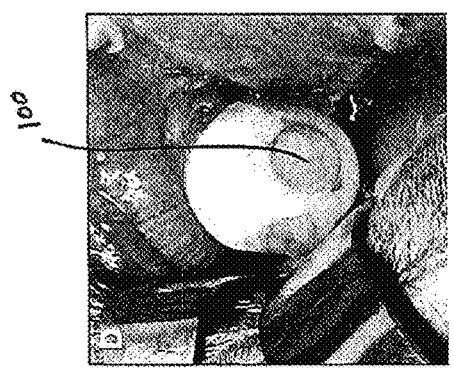
FIG. 6A depicts a schematic view of bone tissue including a cartilage lesion to be replaced by an implant such as the implant of FIG. 1.
Figure 6B:
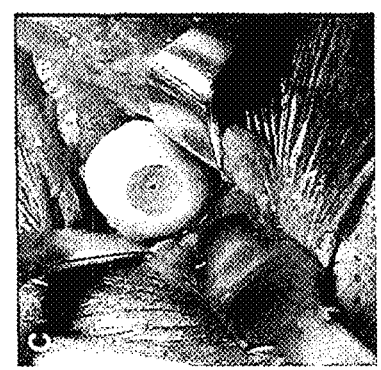
FIG. 6B depicts preparation of a bone bed of the bone tissue of FIG. 6A.
Figure 6C:
FIG. 6C depicts the prepared bone bed of FIG. 6B.
Figure 6D:
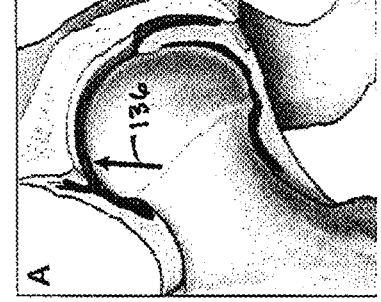
FIG. 6D depicts an implant, such as the implant of FIG. 1 inserted into the prepared bone bed of FIG. 6C.
Figure 6E:
FIG. 6E depicts bone tissue including damaged cartilage to be replaced by an implant such as the implant of FIG. 1.
Figure 6F:
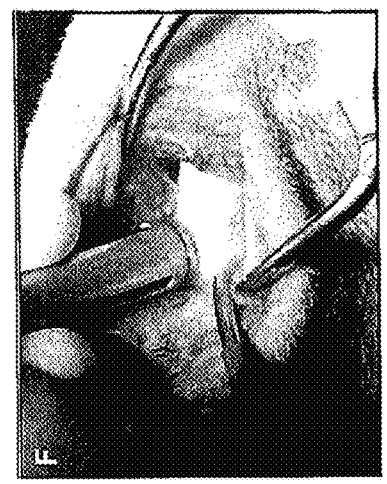
FIG. 6F depicts preparation of a bone bed of the bone tissue of FIG. 6E.
Figure 6G:
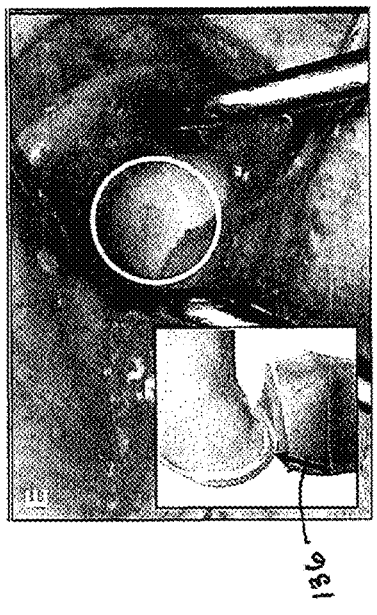
FIG. 6G depicts an implant, such as the implant of FIG. 1 inserted into the prepared bone bed of FIG. 6F.

FIGS. 6A-6G depict use of this technology in different joint spaces, namely in a canine model in the hip (shown in FIGS. 6A, 6B, 6C, and 6D), and a caprine model for osteoarthritis of the knee (shown in FIGS. 6E, 6F, and 6G). These surgical pictures demonstrate the applicability of the approach to resolving complicated cartilage pathology on complex, anatomic geometries. The substantial curvature of each of the joints (as noted by the arrows 136 in FIGS. 6A and 6E) is defined by multiple radii. The implant 100 (shown in FIGS. 6D and 6G) is able to match the curvature and recreate many of the structural and mechanical properties of the native, functioning tissue.

To illustrate the versatility of the implant 100 for various applications, each of FIGS. 7A-7C depicts a different possible configuration of the implant 100 shown in FIG. 1. In each of the configurations shown in FIGS. 7A-7C, the three-dimensional woven and molded fabric 104 is formed in the shape of joint tissues to be repaired. In particular, the woven textile scaffold 104 is formed as a hollow hemisphere having a curved underside 138. Each of FIGS. 7A, 7B, and 7C depicts a cross-section of a different possible configuration of the porous, rigid substrate 108 coupled to the scaffold 104 and configured to support the three-dimensional woven textile scaffold 104 shown in FIG. 1. Each of the various configurations of the substrate 108 is appropriate for implantation at a different site in the body to enable anchoring the implant 100 at a variety of joints to be repaired.

FIG. 7A depicts the substrate 108 substantially formed as a cylinder. The substrate 108 has a bottom 140 that is substantially flat, and a top 144 that is curved to matingly fit with a portion of the curved underside 138 of the scaffold 104. The top 144 of the substrate 108 has a diameter that is smaller than a diameter of the curved underside 138 of the scaffold 104, and the top 144 of the substrate 108 is centered relative to the curved underside 138 of the scaffold 104.

FIG. 7B depicts the substrate 108 including a stem 152 and a head 156. The stem 152 is substantially cylindrical and extends from the bottom 140 of the substrate 108 to the head 156. The stem 152 has a diameter that is smaller than a diameter of the head 156, and the stem 152 is centered relative to the head 156. The head 156 is substantially hemispherical and extends from the top 144 of the substrate 108 to the stem 152. The hemispherical shape of the head 156 is configured to matingly fit with the shape of the curved underside 138 of the scaffold 104 and to contact substantially the entire curved underside 138 of the scaffold 104.

FIG. 7C depicts the substrate 108 substantially formed as a cylinder. The substrate 108 has a bottom 140 that is substantially flat, and a top 144 that is curved to matingly fit with the curved underside 138 of the scaffold 104. The top 144 is shaped to contact substantially the entire curved underside 138 of the scaffold 104.

FIGS. 8A and 8B depict another alternative embodiment of the implant 100. In the embodiment shown in FIGS. 8A and 8B, the bottom 140 of the substrate 108 is substantially as a cylinder, and the top 144 of the substrate is configured to matingly fit with the shape of both the curved underside 138 and a flat underside 148 of the scaffold 104 (shown in FIG. 8B). In other words, the underside of the hollow hemisphere shape of the scaffold 104 includes a concave surface (the curved underside 138) and a flat surface (the flat underside 148) surrounding the concave surface. In the embodiment shown in FIGS. 8A and 8B, the scaffold 104 is attached or bonded to the substrate 108 such that the substrate 108 completely supports the three-dimensional woven textile scaffold 104.

Figure 9B:
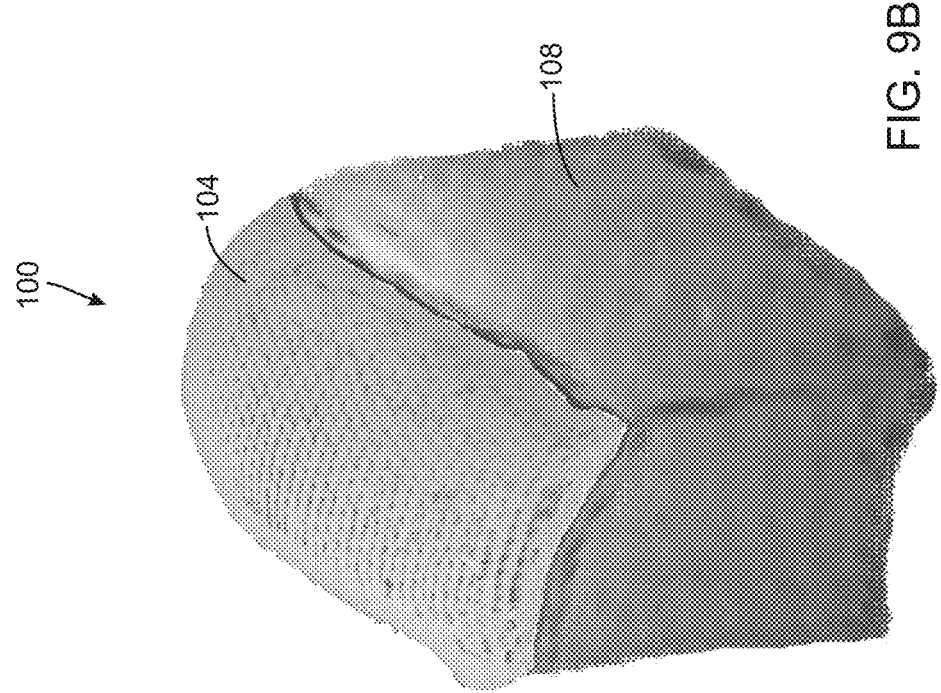
FIG. 9B depicts a cross-sectional view of the cartilage repair implant of FIG. 9A.
Figure 9A:
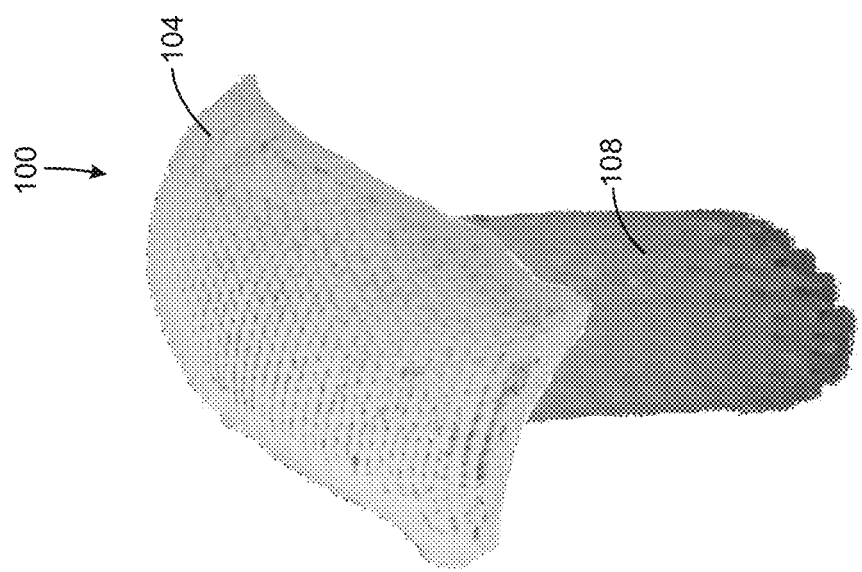
FIG. 9A shows an embodiment of the cartilage repair implant of FIG. 1 configured for knee cartilage repair.

FIGS. 9A and 9B depict additional alternative embodiments of the implant 100. In the embodiments shown in FIGS. 9A and 9B, the scaffold 104 is shaped as a knee condyle. In FIG. 9A, the scaffold 104 is attached to a narrow substrate 108, which does not contact and support an entire underside of the scaffold 104. In contrast, FIG. 9B includes the same scaffold 104 but includes a substrate 108 configured to completely contact and support the underside of the three-dimensional woven textile scaffold 104. Each of FIGS. 9A and 9B depicts complex curvature of the cartilage repair device 100 for replacing, repairing, and regenerating complicated joint anatomy.

Figure 10B:
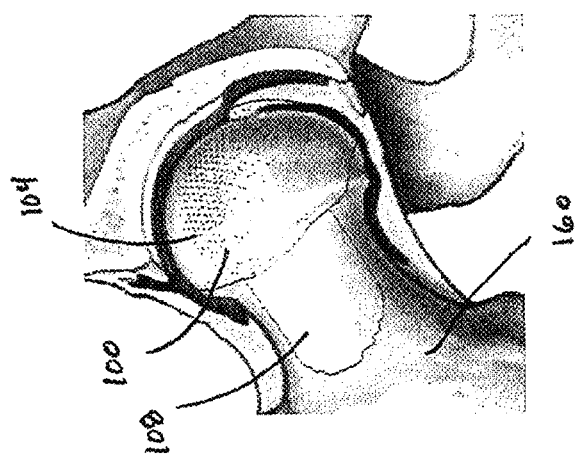
FIG. 10B shows the hip joint after the hip bone tissue has been replaced by the implant such as the cartilage repair implant of FIG. 1.
Figure 10A:
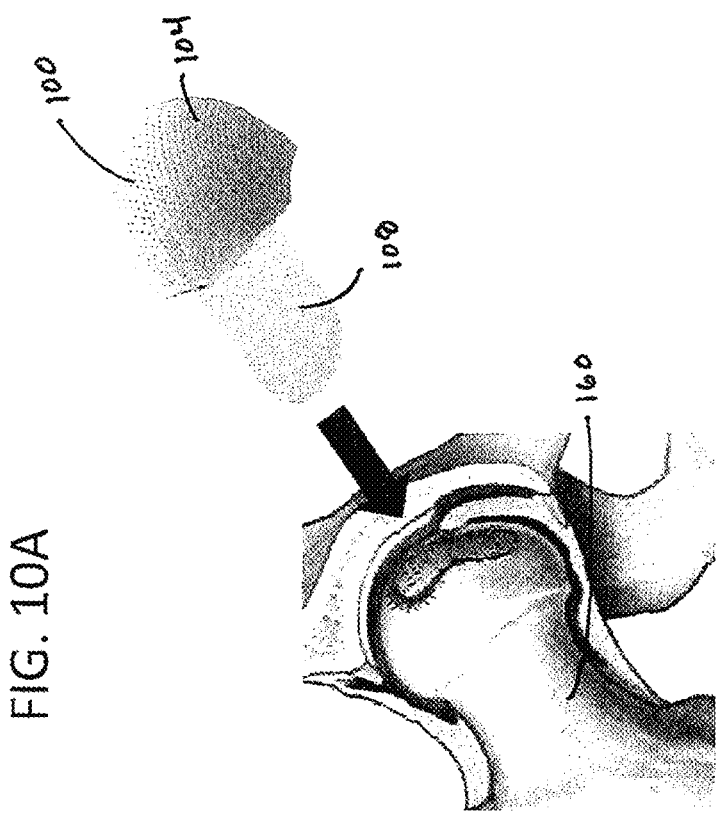
FIG. 10A depicts a hip joint including hip bone tissue to be replaced by an implant such as the cartilage repair implant of FIG. 1.

FIGS. 10A and 10B depict use of the implant 100 for repair of osteoarthritis of the hip. In this example, the cartilage repair device 100 is formed in the shape of a human femoral head. As shown in FIG. 10A, the device 100 is implanted such that the substrate 108 is anchored in the femoral neck 160 of the hip, and, as shown in FIG. 10B, the cartilage repair device 100 replaces the anatomy of the entire femoral head.

Figure 11C:
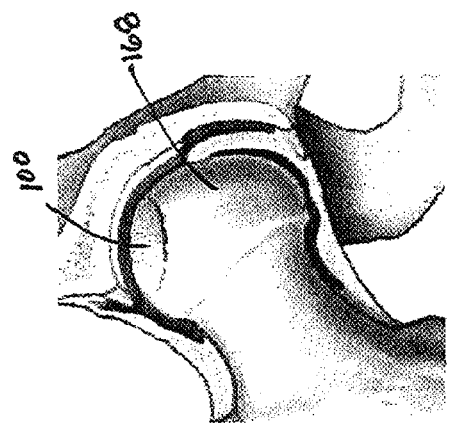
FIG. 11C depicts the hip bone tissue after implantation of the implant of FIG. 11B.
Figure 11B:
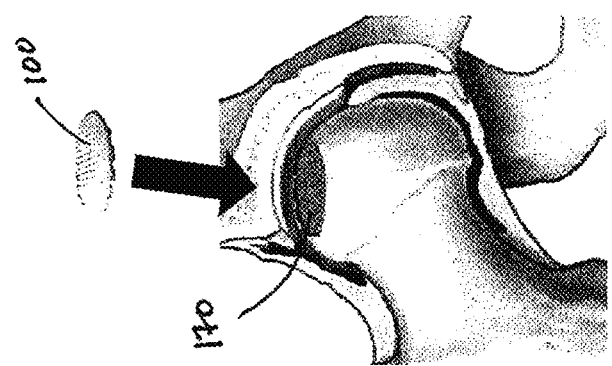
FIG. 11B depicts the hip bone tissue after preparation of a bone bed for implantation of an implant.
Figure 11A:
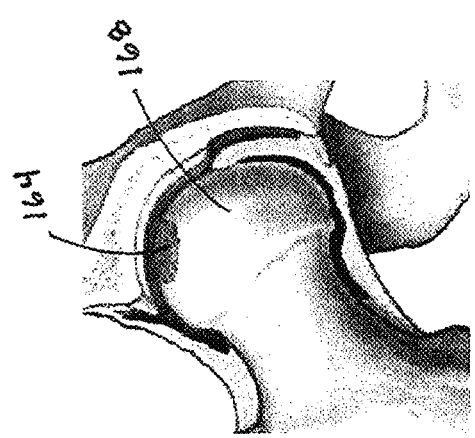
FIG. 11A depicts a hip joint including load bearing hip bone tissue to be replaced by an implant such as the cartilage repair implant of FIG. 1.

FIGS. 11A-11C depict another embodiment of the cartilage repair device 100 configured to repair a smaller lesion than that illustrated in FIG. 10A. FIG. 11A depicts a lesion 164, which is larger than what can be treated using current procedures, located in the load-bearing aspect of the femoral head 168. The defect 164 is debrided to form a regular, controlled defect 170 (shown in FIG. 11B) having a regular shape that encompasses the entire lesion 164. This prepares the site for receipt of the cartilage repair device 100, shown in FIG. 11B. As shown in FIG. 11C, the cartilage repair device 100 is placed in the femoral head 168 to treat the superiorly located cartilage lesion 164.

Figure 12B:
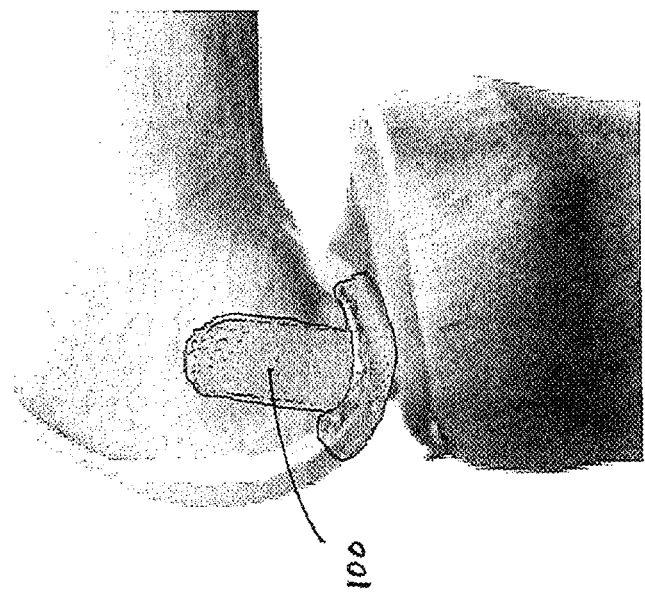
FIG. 12B depicts the knee bone tissue after implantation of the implant of FIG. 12A.
Figure 12A:
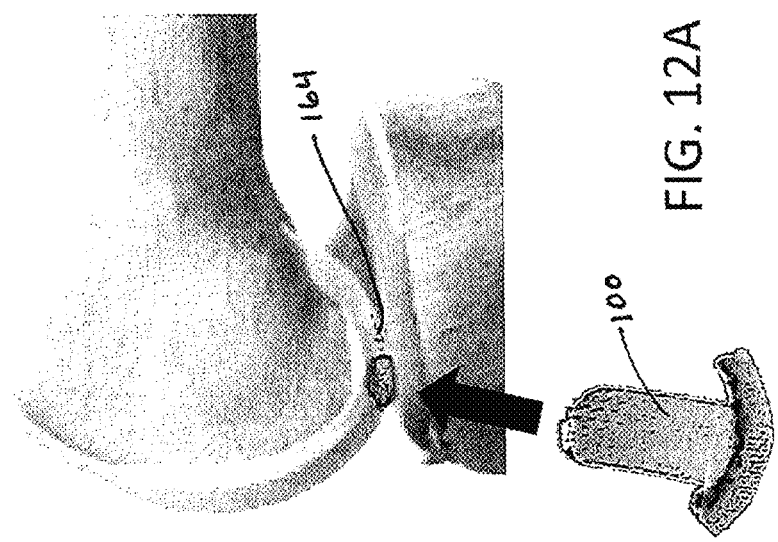
FIG. 12A depicts a knee joint including load bearing knee bone tissue to be replaced by an implant such as the cartilage repair implant of FIG. 1.

FIGS. 12A and 12B demonstrate an application of the cartilage repair device 100 in the knee. Osteoarthritis of the condyle is effectively repaired by removing damaged cartilage in the region around the diseased bone 164 and preparing bone in the condyle, as shown in FIG. 12A. An anatomic shaped cartilage repair implant 100 is then implanted, as shown in FIG. 12B.

Figure 13B:
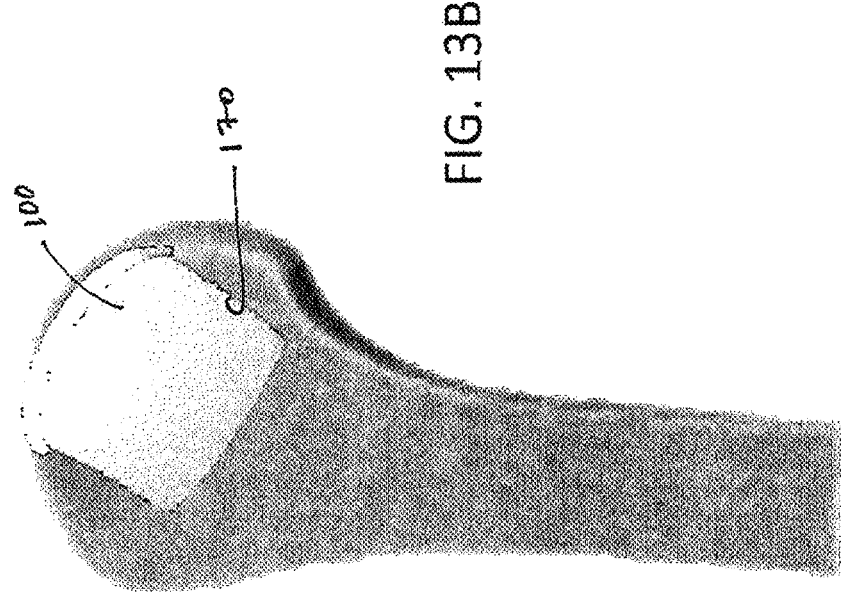
FIG. 13B depicts the bone tissue after implantation of the implant of FIG. 13A.
Figure 13A:
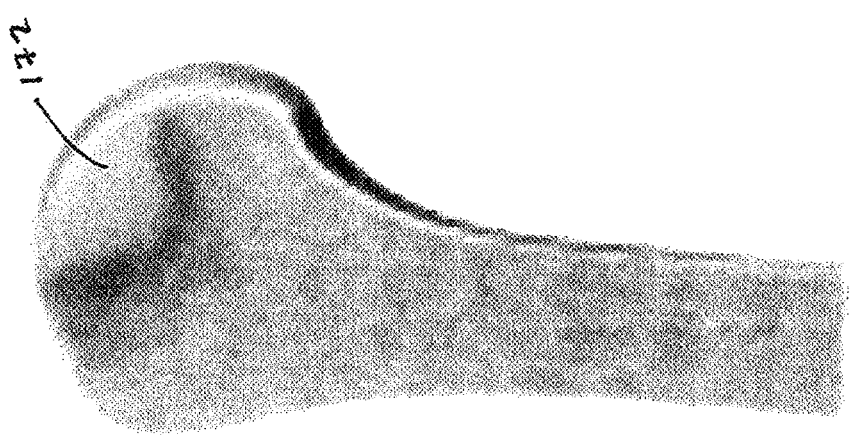
FIG. 13A depicts a humeral head including bone tissue having osteonecrosis to be replaced by an implant such as the cartilage repair implant of FIG. 1.

FIGS. 13A and 13B depict treatment of osteonecrosis of the humeral head. The necrotic bone 172, shown in FIG. 13A, is removed, and the cartilage repair implant 100 is anchored in the defined lesion 170 that was formed by the removal of the necrotic bone 172, as shown in FIG. 13B.

In at least one embodiment, the cartilage repair implant 100 is constructed as follows. The scaffold 104 of the cartilage repair implant 100 is constructed using an orthogonal three-dimensional woven fabric. In particular, a biomedical grade yarn (150 μm in diameter) is woven into a three-dimensional orthogonal structure containing eleven in-plane fiber layers; five layers oriented in the warp (x direction, or 0° or lengthwise in the loom) direction and six layers oriented in the weft (y direction or 90° to the lengthwise fibers) direction. The scaffold 104 contains twenty-four yarns per centimeter in each of the five warp layers, twenty yarns per centimeter in each of the six weft layers and twenty-four yarns per centimeter in the Z-direction. The interconnected internal pores of the scaffold 104 have dimensions of 390 μm×320 μm×104 μm, yielding a total void volume of about 60-70%. After the fabric is woven, the scaffold 104 is cut to near size, and then molded into the shape of the defect using custom-built molds for the geometry in question. Preferably, the material of the scaffold 104 is stabilized using controlled heating to reorganize the molecular state of the polymers that make up the constituent yarns and lock them into an altered physical conformation. This process, known as "heat setting" stabilizes the structure without sacrificing the porosity in each layer, the through porosity, or the designed mechanical properties of the structure. Using any conventional imaging modality (e.g., MRI, CT, or X-Ray), the arthritic defect is precisely mapped.

The substrate 108 of the cartilage repair implant 100 is preferably three-dimensional printed such that it can be easily manufactured to match the geometry/anatomy in question and to completely support the upper three-dimensional woven, textile scaffold 104 of the implant 100. The layers of the substrate 108 are preferably between 200 μm and 500 μm thick, and the strand spacing is preferably between 0.5 and 1.0 mm. Each successive layer is extruded 90 degrees to the previous, again at 1 mm spacing. The total height of the substrate 108 is determined by the number of layers. In this example, 20 layers are extruded, yielding a thickness of the substrate to be about 6.4 mm. The thickness of the cartilage repair implant 100, including both the substrate 108 and the scaffold 104, is about 7 mm. The radius and geometry of the upper face of the scaffold 104 of the implant 100 is manufactured to match the diameter/radius/curvature of the joint surface that is being repaired. The substrate 108 is then, preferably, thermally bonded under microscopic control to the scaffold 104 to create a two-zone cartilage repair implant 100. Preferably, poly(ε-caprolactone) (PCL) is used to manufacture both the substrate 108 and the scaffold 104 due to its slow degradation rate and the ability to maintain appropriate mechanical characteristics over long time periods. The implant 100 is also configured to match the compressive moduli of cartilage to enable immediate functionality while de novo tissue develops in, through, and on the surface of the cartilage repair implant 100. For example, the compressive modulus of the scaffold 104 can be between 200 kPa and 5 MPa.

In at least one alternative embodiment, the cartilage repair implant 100 is constructed as follows. The scaffold 104 of the cartilage repair implant 100 is constructed using an orthogonal three-dimensional woven fabric. In particular, a biomedical grade yarn (150 μm in diameter) is woven into a three-dimensional orthogonal structure containing eleven in-plane fiber layers; five layers oriented in the warp (x direction, or 0° or lengthwise in the loom) direction and six layers oriented in the weft (y direction or 90° to the lengthwise fibers) direction. The scaffold 104 contains twenty-four yarns per centimeter in each of the five warp layers, twenty yarns per centimeter in each of the six weft layers and twenty-four yarns per centimeter in the Z-direction. The interconnected internal pores of the scaffold 104 have dimensions of 390 μm×320 μm×104 μm, yielding a total void volume of about 60-70%. After the fabric is woven, the scaffold 104 is cut to near size, and then molded into the shape of the defect using custom-built molds for the geometry in question. Preferably, the material of the scaffold 104 is stabilized using controlled heating to reorganize the molecular state of the polymers that make up the constituent yarns and lock them into an altered physical conformation. This process, known as "heat setting" stabilizes the structure of the scaffold 104 without sacrificing the porosity in each layer, the through porosity, or the designed mechanical properties of the structure. Using any conventional imaging modality (e.g., MRI, CT, or X-Ray), the arthritic defect is precisely mapped.

The substrate 108 of the cartilage repair implant 100 is preferably three-dimensional printed such that it matches the geometry of a prepared anchoring hole made in the bone. The layers of the substrate 108 are preferably between 200 μm and 500 μm thick, and the strand spacing is preferably between 0.5 and 1.0 mm. Each successive layer is extruded 90 degrees to the previous, again at 1 mm spacing. The substrate 108 is then, preferably, thermally bonded under microscopic control to the three-dimensional woven scaffold 104 to create a bilayered (i.e., two distinct zones) cartilage repair implant 100. Preferably, poly(ε-caprolactone) (PCL) is used to manufacture both the scaffold 104 and the substrate 108 due to its slow degradation rate and the ability to maintain appropriate mechanical characteristics over long time periods. The implant 100 is also configured to match the compressive moduli of cartilage to enable immediate functionality while de novo tissue develops in, through, and on the surface of the cartilage repair implant 100.

The total height of the substrate 108 is determined by the number of layers. In this example, 30 layers are extruded, yielding a thickness of the substrate 108 to be about 9.6 mm. The three-dimensional printed substrate 108 matches the curvature of the woven scaffold 104 at an attachment point where the substrate 108 and the scaffold 104 are joined together. The three-dimensional printed substrate 108 is extruded with a circular cross section and is 10 mm in diameter. A hole is prepared in the bone using known techniques such as with the use of a drill or end mill that is also 10 mm in diameter or slightly undersized. The arthritic area is then debrided, and the substrate 108 is press fit and therefore anchored into the bone such that the scaffold 104 completely replaces degenerated surfaces, thereby restoring joint congruity. The total thickness of the cartilage repair implant 100 is about 11 mm.

In at least one alternative embodiment, the cartilage repair implant 100 is constructed as follows. The scaffold 104 of the cartilage repair implant 100 is constructed from an orthogonal three-dimensional woven fabric. In particular, a biomedical grade yarn (150 μm in diameter) is woven into a three-dimensional orthogonal structure eleven in-plane fiber layers; five layers are oriented in the warp (0° or lengthwise in the loom) direction and six layers are oriented in the weft (90° to the lengthwise fibers) direction. The structure contained twenty-four yarns per centimeter in each of the five warp layers, twenty yarns per centimeter in each of the six weft layers and twenty-four yarns per centimeter in the Z-direction. Prior to weaving, the warp fiber bundles are coated with a lentivirus encoding transforming growth factor—beta (TGF-ß) to induce cartilaginous differentiation of cells migrating onto the scaffold 104 after implantation.

The substrate 108 is three-dimensional printed with a 320 µm layer thickness and 1 mm spacing between extruded filaments. Each successive layer is extruded 90 degrees to the previous, again at 1 mm spacing. The total height of the substrate 108 is determined by the number of layers. In this example, 10 layers are extruded, yielding a thickness of the substrate 108 to be about 3.2 mm. The thickness of the cartilage repair implant 100, including both the substrate 108 and the scaffold 104, is about 4 mm. The upper surface of the substrate 108 is designed and manufactured to match the curvature of the surface in need of repair (e.g., femoral head or knee condyle). The printed layer of the substrate 108 is coated with bone morphogenetic factor 2 (BMP-2) or a lentivirus encoding for BMP-2 to promote osteogenic differentiation of the endogenous stem cells migrating into the structure and therefore anchoring of the construct into the underlying bone.

As in the previous embodiments, the interconnected internal pores of the scaffold 104 have dimensions of 390 µm×320 µm×104 µm, yielding a total void volume of about 60-70%. After the fabric of the scaffold 104 is woven, the scaffold 104 is bonded to the three-dimensional printed substrate 108, preferably thermally. Preferably, poly(ε-caprolactone) (PCL) is used to manufacture both the scaffold 104 and the substrate 108 due to its slow degradation rate and the ability to maintain appropriate mechanical characteristics over long time periods. The implant 100 is also designed to match the compressive moduli of cartilage to enable immediate functionality while de novo tissue develops in, through, and on the surface of the cartilage repair implant 100.

After the substrate 108 and the scaffold 104 are connected to one another, the resulting two zone implant 100 is cut to near size, lyophilized, and sterilized using non-heat sterilization methods (e.g., low temperature ethylene oxide sterilization). The implant 100 is removed from packaging at the time of surgery, cut to the shape of the defect and then placed into the defect with the osteogenic side on the prepared bone bed.

In at least one alternative embodiment, a cartilage repair implant 100 is constructed for cartilage repair in a canine hip. The scaffold 104 is constructed using an orthogonal three-dimensional woven fabric manufactured using a biomedical grade yarn (150 µm in diameter), which is woven into a three-dimensional orthogonal structure containing eleven in-plane fiber layers; five layers oriented in the warp (x direction, or 0° or lengthwise in the loom) direction and six layers oriented in the weft (y direction or 90° to the lengthwise fibers) direction. The scaffold 104 contains twenty-four yarns per centimeter in each of the five warp layers, twenty yarns per centimeter in each of the six weft layers and twenty-four yarns per centimeter in the Z-direction. The interconnected internal pores of the scaffold 104 have dimensions of 390 µm×320 µm×104 µm, yielding a total void volume of about 60-70% and a total thickness of about 700 microns. After the fabric is woven, the scaffold 104 is cut to near size, in this case, a 10 mm diameter disc.

The substrate 108 of the implant 100 is three-dimensional printed to a total height of about 2 mm with a diameter of 10 mm, identical to that of the textile scaffold 104 of the implant 100. The filaments in the layers of the substrate 108 are printed at 320 µm thick, and the strand spacing is 1.0 mm. Each successive layer of the substrate 108 is extruded 90 degrees to the previous, again at 1 mm spacing. The three-dimensional printed substrate 108 is configured and printed to match the curvature of the arthritic cartilage to be replaced and regenerated. The substrate 108 is then, preferably, thermally bonded under microscopic control to the three-dimensional woven scaffold 104 to create a bilayered (i.e., two distinct zones) structure to create the cartilage repair implant 100. Poly(ε-caprolactone) (PCL) is used to manufacture both the scaffold 104 and the substrate 108 due to its slow degradation rate and the ability to maintain appropriate mechanical characteristics over long time periods.

The implant 100 is also configured to match the compressive moduli of cartilage to enable immediate functionality while de novo tissue develops in, through, and on the surface of the cartilage repair implant 100. For example, the compressive modulus of the scaffold 104 can be between 200 kPa and 5 MPa. To test the efficacy of the implant 100, a canine model of osteoarthritis can be used to test the bilayer/two zone structure of the implant 100. As shown in FIG. 14A, data from one such test indicate that twenty-four hour activity levels (significant movements) averaged over a two week period indicate less activity one month post-op (after the implantation operation) relative to pre-op (before the implantation operation) activity levels. As shown in FIG. 14B, six month activity levels indicate a return to normal activity in experimental animals that received the bilayer/two zone implant 100. As shown in FIGS. 14C and 14D, pressure sensitive walkway studies reveal a return to pre-operative, "normal" kinematics by three months as measured by Peak Vertical Force (PVF) (shown in FIG. 14C) and hind limb propel force (shown in FIG. 14D). SI, shown in FIGS. 14C and 14D, refers to "symmetry index," which measures lameness by normalizing values obtained from the treated limb to the contralateral limb for a given measure. A value of 0 means there is no difference between operative and contralateral control and a value of −200 means complete lameness.

FIGS. 14E and 14F show examples at necropsy of control (shown in FIG. 14E) and experimental (shown in FIG. 14F) operated hips six months after the implantation operation. The degraded cartilage in the arthritic control shown in FIG. 14E illustrates the efficacy of the smooth repair in the experimental group using the bilayered implant 100 shown in FIG. 14F. Gross evaluation of the joints of the experimental group at six months at necropsy reveals integration with host tissue, with no signs of cavitation or further erosion of the cartilage surface while maintaining the normal anatomic curvature of the femoral head. These data indicate that the functional biomimetic three-dimensional woven textile scaffold 104, bonded to the three-dimensional printed anchoring substrate 108 is instrumental in achieving successful clinical results.

In at least one alternative embodiment, a cartilage repair implant 100 is constructed for repair of osteonecrosis of the humeral head. The necrotic bone can be identified in the patient via standard magnetic resonance or computed tomography imaging. Once the necrotic zone is identified, surgical planning is conducted to determine the margin of necrotic bone that needs to be removed while maximally preserving healthy bone stock. Custom guides are then designed using free form modeling software and then manufactured to guide removal of the diseased tissue.

The implant 100 is configured to match the defect created with the guided tools. For this example, after locating the defect from the guiding tools, a depth-stopped cannulated end mill is passed over a k-wire for drilling out necrotic bone, resulting in a 15 mm diameter by 15 mm deep cut. An appropriate-sized bilayered implant 100 manufactured in a similar manner to what has been presented in the previous embodiments is pressed into place.

The present disclosure should be considered as illustrative and not restrictive in character. It is understood that only certain embodiments have been presented and that all changes, modifications, and further applications that come within the spirit of the disclosure are desired to be protected.

What is claimed is:

1. A method for repairing a cartilage lesion, the method comprising:
   bringing a three-dimensional porous substrate into direct contact with prepared bone, wherein:
   the three-dimensional porous substrate is fixedly coupled to a three-dimensional scaffold, and
   the three-dimensional scaffold comprises a plurality of layers of woven fibers.

2. The method of claim 1, wherein bringing the three-dimensional porous substrate into direct contact with prepared bone includes press fitting the three-dimensional porous substrate into a matingly configured site of the prepared bone.

3. The method of claim 1, wherein bringing the three-dimensional porous substrate into direct contact with prepared bone includes securing the three-dimensional porous substrate to the prepared bone without any additional fastening means.

4. The method of claim 1, wherein the three-dimensional porous substrate is configured to integrate into the prepared bone.

5. The method of claim 1, wherein:
   the plurality of layers of woven fibers includes:
     in-plane warp fibers oriented in a first direction;
     weft fibers oriented in a second direction orthogonal to the first direction; and
     binding fibers oriented in a third direction orthogonal to the first and second directions, and
   the weft fibers and the binding fibers are arranged between the in-plane warp fibers.

6. The method of claim 1, wherein the three-dimensional scaffold is a three-dimensional warp interlock fabric.

7. The method of claim 1, wherein:
   the plurality of layers of woven fibers includes:
     a warp layer comprising in-plane warp fibers oriented in a first direction;
     a weft layer comprising weft fibers oriented in a second direction orthogonal to the first direction; and
     a binding layer comprising binding fibers oriented in a third direction orthogonal to the first and second directions, and
   the three-dimensional scaffold includes five warp layers and six weft layers interconnected by fibers oriented in the third direction.

8. The method of claim 1, wherein:
   the plurality of layers of woven fibers includes:
     a warp layer comprising in-plane warp fibers oriented in a first direction;
     a weft layer comprising weft fibers oriented in a second direction orthogonal to the first direction; and
     a binding layer comprising binding fibers oriented in a third direction orthogonal to the first and second directions, and
   the three-dimensional scaffold includes twenty-four yarns per centimeter in each of the warp layers, fifteen to twenty yarns per centimeter in each of the weft layers and twenty-four yarns per centimeter oriented in the third direction.

9. The method of claim 1, wherein at least one of the three-dimensional scaffold and the three-dimensional substrate has a void volume of at least 50%.

10. The method of claim 1, wherein a compressive modulus of the three-dimensional scaffold is between approximately 200 kPa and approximately 5 MPa.

11. The method of claim 1, wherein the three-dimensional porous substrate is comprised of extruded filament that form struts, each strut having a diameter of approximately 150 μm to approximately 500 μm.

12. The method of claim 1, wherein:
    the three-dimensional porous substrate comprises a first three-dimensionally printed layer and a second three-dimensionally printed layer arranged on top of the first three-dimensionally printed layer,
    the first three-dimensionally printed layer includes a first plurality of extruded struts oriented in a first strut direction,
    the second three-dimensionally printed layer includes a second plurality of extruded struts oriented in a second strut direction, and
    the second strut direction is angled approximately 30 degrees to approximately 120 degrees relative to the first strut direction.

13. The method of claim 1, wherein:
    at least a portion of at least one of the three-dimensional scaffold and the three-dimensional porous substrate is coated with at least one biological agent, and
    the at least one biological agent is selected from the group consisting of collagen, hyaluronic acid, alginate, agarose, chitosan, gelatin, laminin, fibronectin, fibrin, proteoglycan, cartilage oligomeric matrix protein, hyaluronic acid, collagen type I, collagen type II, peptide sequences, self-assembling peptides, anti-inflammatory drugs, bone morphogenetic proteins and other cytokines, cytokines inhibitors, cartilage-derived matrix, demineralized bone matrix and/or other decellularized extracellular matrix-derived tissues.

14. The method of claim 1, wherein:
    at least a portion of the woven fibers are coated with at least one inorganic matrix, and
    the at least one inorganic matrix is selected from the group consisting of hydroxyapatite, calcium phosphate, calcium carbonate, alumina, zirconia, yttria-stabilized zirconia, silicon nitride-based materials, bioactive glass, and/or glass ceramics.

15. The method of claim 1, wherein:
    at least a portion of the three-dimensional scaffold is at least partially filled with a biomaterial gel, and
    the biomaterial gel is selected from the group consisting of collagen, hyaluronic acid, alginate, agarose, chitosan, gelatin, laminin, fibronectin, interpenetrating networks containing fully biologic materials, fully synthetic, or mixtures thereof and/or fibrin or combinations thereof.

16. The method of claim 1, wherein at least a portion of the woven fibers are coated with virus, plasmids, or DNA adapted to transfect or transduce cells within the implant for cartilage and/or bone induction.

17. The method of claim 1, wherein:
at least one cell is embedded within at least one of the three-dimensional scaffold and the three-dimensional porous substrate,
the at least one cell is selected from the group consisting of primary cells, undifferentiated progenitor cells, stem cells, induced pluripotent stem cells and combinations thereof,
the undifferentiated progenitor cells or stem cells are selected from the group consisting of stem or progenitor cells derived from adipose tissue, bone marrow, synovium, muscle, bone, cord blood, periosteum, and combinations thereof, and
the primary cells are selected from the group consisting of chondrocytes, osteoblasts, fibroblasts, fibrochondrocytes, and combinations thereof.

18. The method of claim 1, wherein:
each of the woven fibers and the three-dimensional porous substrate are formed of a biocompatible material, and
the biocompatible material is selected from the group consisting of an absorbable material, a non-absorbable material, and combinations thereof, wherein:
the non-absorbable material is selected from the group consisting of a polytetrafluoroethylene (PTFE), an expanded PTFE (ePTFE), a polyamide, a nylon, a polysulfone, a cellulosic, an acrylic, polyvinyl alcohol, carbon, ceramic, a metal, an acrylic, a polycarbonate, a polyester, a polyether, a poly(ether ketone), a poly(ether ether ketone), a poly(ethylene terephthalate), a poly(methyl(meth)acrylate), a polyolefin, a polysulfone, a polyurethane, and
the absorbable material is selected from the group consisting of a polyglycolic acid (PGA), a polylactic acid (PLA), a polyglycolide-lactide, a polycaprolactone, a polydioxanone, a polyoxalate, a polyanhydride, a poly(phosphoester), catgut suture, collagen, silk, alginate, agarose, chitin, chitosan, hydroxyapatite, bioabsorbable calcium phosphate, hyaluronic acid, elastin, a polyorthoester, a poly(amino acid), a pluronic/F-12, a poly(ethylene oxide)/poly(ethylene glycol) (PEO/PEG), collagen, gelatin, fibrin, hyaluronic acid, a proteoglycan, elastin, and combinations thereof.

19. The method of claim 1, wherein:
the three-dimensional scaffold includes a plurality of interstices formed within, and
each of the interstices defines a pore size of approximately 50 μm to approximately 1,000 μm.

20. The method of claim 1, wherein at least one of the three-dimensional scaffold and the three-dimensional porous substrate is formed by a plurality of elements, each element of the plurality of elements having a diameter of approximately 25 μm to approximately 300 μm.

21. A method for introducing a cartilage repair implant in a cartilage lesion, the method comprising:
locating a cartilage lesion in a joint;
enlarging the cartilage lesion;
preparing a bone bed surrounding the perimeter of the cartilage lesion to receive a three-dimensional porous substrate of the cartilage repair implant;
inserting the three-dimensional porous substrate of the cartilage repair implant into the prepared bone bed such that the three-dimensional porous substrate and a three-dimensional scaffold fixedly coupled to the porous substrate of the cartilage repair implant completely fill the enlarged cartilage lesion.

22. The method of claim 21, wherein inserting the three-dimensional porous substrate of the cartilage repair implant into the prepared bone bed includes bringing the three-dimensional porous substrate into direct contact with the prepared bone bed.

23. The method of claim 21, wherein inserting the three-dimensional porous substrate of the cartilage repair implant into the prepared bone bed includes press fitting the three-dimensional porous substrate into a matingly configured site of the prepared bone bed.

24. The method of claim 21, wherein inserting the three-dimensional porous substrate of the cartilage repair implant into the prepared bone bed includes securing the three-dimensional porous substrate to the prepared bone bed without any additional fastening means.

25. The method of claim 21, wherein the three-dimensional porous substrate is configured to integrate into the prepared bone bed.

26. The method of claim 21, wherein the cartilage repair implant is molded into a shape configured to matingly fit with the enlarged cartilage lesion and sized to fit with the prepared bone bed.

27. A method of repairing joint tissues in a subject, the method comprising:
locating a site in the joint tissues in need of repair, the site having native anatomic curvature;
removing joint tissues at the site and preparing a bone bed surrounding the perimeter of the site to receive an implant;
inserting the implant into the site, including:
bringing a three-dimensional porous substrate of the implant into contact with the prepared bone bed; and
recreating the native anatomic curvature of the joint with a three-dimensional scaffold of the implant,
wherein the three-dimensional scaffold is fixedly coupled to the three-dimensional porous substrate.

28. The method of claim 27, wherein the three-dimensional scaffold comprises at least three layers of woven fibers.

29. The method of claim 28, wherein:
the plurality of layers of woven fibers includes:
in-plane warp fibers oriented in a first direction;
weft fibers oriented in a second direction orthogonal to the first direction; and
binding fibers oriented in a third direction orthogonal to the first and second directions, and
the weft fibers and the binding fibers are arranged between the in-plane warp fibers.

30. The method of claim 27, wherein bringing the three-dimensional porous substrate into contact with prepared bone bed includes press fitting the three-dimensional porous substrate into a matingly configured site of the prepared bone bed.

31. The method of claim 27, wherein:
the three-dimensional porous substrate comprises a first three-dimensionally printed layer and a second three-dimensionally printed layer arranged on top of the first three-dimensionally printed layer,
the first three-dimensionally printed layer includes a first plurality of extruded struts oriented in a first strut direction,
the second three-dimensionally printed layer includes a second plurality of extruded struts oriented in a second strut direction, and
the second strut direction is angled approximately 30 degrees to approximately 120 degrees relative to the first strut direction.

* * * * *